(12) United States Patent
Ikeda et al.

(10) Patent No.: US 7,445,915 B2
(45) Date of Patent: Nov. 4, 2008

(54) MUTANT ISOPROPYLMALATE ISOMERASE

(75) Inventors: Masato Ikeda, Nagano (JP); Mikiro Hayashi, Machida (JP); Junko Ohnishi, Nagano (JP); Satoshi Mitsuhashi, Hofu (JP); Hiroshi Mizoguchi, Machida (JP); Satoshi Nakagawa, Machida (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 227 days.

(21) Appl. No.: 10/508,313

(22) PCT Filed: Mar. 19, 2003

(86) PCT No.: PCT/JP03/03353

§ 371 (c)(1),
(2), (4) Date: Sep. 20, 2004

(87) PCT Pub. No.: WO03/078620

PCT Pub. Date: Sep. 25, 2003

(65) Prior Publication Data

US 2005/0130276 A1 Jun. 16, 2005

(30) Foreign Application Priority Data

Mar. 19, 2002 (JP) ............................ 2002-076228

(51) Int. Cl.
C12N 13/04 (2006.01)
C12P 13/08 (2006.01)
C12P 13/10 (2006.01)
C12P 13/14 (2006.01)
C12P 13/22 (2006.01)
C12P 13/24 (2006.01)
C07H 21/04 (2006.01)

(52) U.S. Cl. ................. 435/106; 435/107; 435/108; 435/110; 435/114; 435/115; 435/183; 435/233; 435/252.3; 435/252.32; 435/253.1; 536/23.2

(58) Field of Classification Search ............... None
See application file for complete search history.

(56) References Cited

U.S. PATENT DOCUMENTS 7,141,663 B2 * 11/2006 Zelder et al. ............... 536/23.7

FOREIGN PATENT DOCUMENTS

| EP | 1108790 A2 | 6/2001 |
|---|---|---|
| WO | WO 03/040681 | 5/2003 |
| WO | WO 03/054179 | 7/2003 |

OTHER PUBLICATIONS

WO200100843-A2 Pompejus et al. *Corynebactriumglutamicum* genes that encode metabolic pathway proteins.*
Nakayama et al. Microbial production of Essential amino acids with *Corynebactrium glutamicum* mutants. Advances in Experimental Medicine and Biology, 1978 vol. 105:649-661.*
Patek et al. Leucine synthesisi in *Corynebactrium glutamicum*: Enzyme activities, Structure of leuA, and effect of leuA Inactivation on Lysine Synthesis. Applied and Environmental Microbiology Jan. 1994, vol. 60, p. 133-140.*
Schrumpf et al A Functional Split pathway for Lysine synthesis in *Corynebactrium glutamicum*. Journal of Bacteriology, Jul. 1991, vol. 173 pNo. 14, p. 4510-4516.*
Hermann Sahm, et al.; "Isolation and Prominent Characteristics of an L-Lysine Hyperproducing Strain of *Corynebacterium glutamicum*"; Appl., Microbiol. Biotechnol., vol. 37, 1992, pp. 566 to 571.
Hermann Sahm, et al: "Leucine Synthesis in *Corynebacterium glutamicum*: Enzyme Activities, Structure of Leua, and Effect of Leua Inactivation on Lysine Synthesis"; Appl. Microbiol. Biotechnol, vol. 60, No. 1, 1994, pp. 133-140.
English translation of International Preliminary Examination Report dated Dec. 9, 2004 issued in PCT/JP2003/003353.
Hayashi et al, A *leuC* mutation leading to increased L-lysine production and *rel*-independent global expression changes in *Corynebacterium glutamicum*, Appl Microbiol Biotechnol, 72, 783-9 (2006).

* cited by examiner

*Primary Examiner*—Kathleen Kerr Bragdon
*Assistant Examiner*—Kagnew H. Gebreyesus
(74) *Attorney, Agent, or Firm*—Nixon & Vanderhye P.C.

(57) ABSTRACT

The present invention provides a polypeptide comprising an amino acid sequence in which at least one amino acid is deleted, substituted or added in an amino acid sequence of isopropylmalate isomerase derived from a microorganism belonging to coryneform bacteria, wherein a coryneform bacterium which produces the polypeptide comprising the amino acid sequence as the sole isopropylmalate isomerase exhibits a partial leucine requirement in a minimal medium; a DNA encoding the polypeptide, a recombinant DNA comprising the DNA, a microorganism transformed with the recombinant DNA, and a process for producing an L-amino acid using the microorganism.

12 Claims, No Drawings

SEQUENCE LISTING

```
<160> NUMBER OF SEQ ID NOS: 8

<210> SEQ ID NO 1
<211> LENGTH: 481
<212> TYPE: PRT
<213> ORGANISM: Corynebacterium glutamicum ATCC13032

<400> SEQUENCE: 1

Met Thr Ser Pro Val Glu Asn Ser Thr Ser Thr Glu Lys Leu Thr Leu
 1               5                  10                  15

Ala Glu Lys Val Trp Arg Asp His Val Val Ser Lys Gly Glu Asn Gly
            20                  25                  30

Glu Pro Asp Leu Leu Tyr Ile Asp Leu Gln Leu Leu His Glu Val Thr
        35                  40                  45
```

-continued

```
Ser Pro Gln Ala Phe Asp Gly Leu Arg Met Thr Gly Arg Lys Leu Arg
     50                   55                  60

His Pro Glu Leu His Leu Ala Thr Glu Asp His Asn Val Pro Thr Glu
 65                  70                  75                  80

Gly Ile Lys Thr Gly Ser Leu Leu Glu Ile Asn Asp Lys Ile Ser Arg
                 85                  90                  95

Leu Gln Val Ser Thr Leu Arg Asp Asn Cys Glu Glu Phe Gly Val Arg
            100                 105                 110

Leu His Pro Met Gly Asp Val Arg Gln Gly Ile Val His Thr Val Gly
            115                 120                 125

Pro Gln Leu Gly Ala Thr Gln Pro Gly Met Thr Ile Val Cys Gly Asp
130                 135                 140

Ser His Thr Ser Thr His Gly Ala Phe Gly Ser Met Ala Phe Gly Ile
145                 150                 155                 160

Gly Thr Ser Glu Val Glu His Val Met Ala Thr Gln Thr Leu Pro Leu
                165                 170                 175

Lys Pro Phe Lys Thr Met Ala Ile Glu Val Thr Gly Glu Leu Gln Pro
            180                 185                 190

Gly Val Ser Ser Lys Asp Leu Ile Leu Ala Ile Ile Ala Lys Ile Gly
            195                 200                 205

Thr Gly Gly Gln Gly Tyr Val Leu Glu Tyr Arg Gly Glu Ala Ile
210                 215                 220

Arg Lys Met Ser Met Asp Ala Arg Met Thr Met Cys Asn Met Ser Ile
225                 230                 235                 240

Glu Ala Gly Ala Arg Ala Gly Met Ile Ala Pro Asp Gln Thr Thr Phe
                245                 250                 255

Asp Tyr Val Glu Gly Arg Glu Met Ala Pro Lys Gly Ala Asp Trp Asp
            260                 265                 270

Glu Ala Val Ala Tyr Trp Lys Thr Leu Pro Thr Asp Glu Gly Ala Thr
            275                 280                 285

Phe Asp Lys Val Val Glu Ile Asp Gly Ser Ala Leu Thr Pro Phe Ile
290                 295                 300

Thr Trp Gly Thr Asn Pro Gly Gln Gly Leu Pro Leu Gly Glu Ser Val
305                 310                 315                 320

Pro Ser Pro Glu Asp Phe Thr Asn Asp Asn Lys Ala Ala Ala Glu
                325                 330                 335

Lys Ala Leu Gln Tyr Met Asp Leu Val Pro Gly Thr Pro Leu Arg Asp
            340                 345                 350

Ile Lys Ile Asp Thr Val Phe Leu Gly Ser Cys Thr Asn Ala Arg Ile
            355                 360                 365

Glu Asp Leu Gln Ile Ala Ala Asp Ile Leu Lys Gly His Lys Ile Ala
370                 375                 380

Asp Gly Met Arg Met Met Val Val Pro Ser Ser Thr Trp Ile Lys Gln
385                 390                 395                 400

Glu Ala Glu Ala Leu Gly Leu Asp Lys Ile Phe Thr Asp Ala Gly Ala
                405                 410                 415

Glu Trp Arg Thr Ala Gly Cys Ser Met Cys Leu Gly Met Asn Pro Asp
            420                 425                 430

Gln Leu Lys Pro Gly Glu Arg Ser Ala Ser Thr Ser Asn Arg Asn Phe
            435                 440                 445

Glu Gly Arg Gln Gly Pro Gly Gly Arg Thr His Leu Val Ser Pro Ala
450                 455                 460
```

```
Val Ala Ala Ala Thr Ala Ile Arg Gly Thr Leu Ser Ser Pro Ala Asp
465                 470                 475                 480

Ile

<210> SEQ ID NO 2
<211> LENGTH: 197
<212> TYPE: PRT
<213> ORGANISM: Corynebacterium glutamicum ATCC13032

<400> SEQUENCE: 2

Met Glu Lys Phe Thr Thr Tyr Thr Gly Val Gly Val Pro Leu Gln Arg
1               5                   10                  15

Ser Asn Val Asp Thr Asp Gln Ile Ile Pro Ala Val Tyr Leu Lys Arg
                20                  25                  30

Val Thr Arg Thr Gly Phe Glu Asp Gly Leu Phe Ser Asn Trp Arg Gln
            35                  40                  45

Asn Asp Pro Asn Phe Val Leu Asn Thr Asp Thr Tyr Lys Asn Gly Ser
        50                  55                  60

Val Leu Val Ala Gly Pro Asp Phe Gly Thr Gly Ser Ser Arg Glu His
65                  70                  75                  80

Ala Val Trp Ala Leu Met Asp Tyr Gly Phe Arg Ala Val Phe Ser Ser
                85                  90                  95

Arg Phe Ala Asp Ile Phe Arg Gly Asn Ser Gly Lys Ala Gly Met Leu
                100                 105                 110

Thr Gly Ile Met Glu Gln Ser Asp Ile Glu Leu Leu Trp Lys Leu Met
            115                 120                 125

Glu Gln Thr Pro Gly Leu Glu Leu Thr Val Asn Leu Glu Lys Gln Ile
        130                 135                 140

Val Thr Ala Gly Asp Val Val Ile Ser Phe Glu Val Asp Pro Tyr Ile
145                 150                 155                 160

Arg Trp Arg Leu Met Glu Gly Leu Asp Asp Ala Gly Leu Thr Leu Arg
                165                 170                 175

Lys Leu Asp Glu Ile Glu Asp Tyr Glu Ala Lys Arg Pro Ala Phe Lys
                180                 185                 190

Pro Arg Thr Asn Ala
        195

<210> SEQ ID NO 3
<211> LENGTH: 1443
<212> TYPE: DNA
<213> ORGANISM: Corynebacterium glutamicum ATCC13032

<400> SEQUENCE: 3 atg acc agc ccc gtg gag aac agc acc tca act gag aag ctg acc ctg      48
Met Thr Ser Pro Val Glu Asn Ser Thr Ser Thr Glu Lys Leu Thr Leu
1               5                   10                  15 gca gag aag gtg tgg cgc gac cat gtc gtg tcc aag gga gaa aac ggc      96
Ala Glu Lys Val Trp Arg Asp His Val Val Ser Lys Gly Glu Asn Gly
                20                  25                  30 gag ccc gac ctc ctc tac atc gac ctg cag ctg ctg cat gaa gtg acc     144
Glu Pro Asp Leu Leu Tyr Ile Asp Leu Gln Leu Leu His Glu Val Thr
            35                  40                  45 tca cca cag gca ttt gac ggc ctg cgc atg acc ggc cgt aaa ctg cgc     192
Ser Pro Gln Ala Phe Asp Gly Leu Arg Met Thr Gly Arg Lys Leu Arg
        50                  55                  60 cac cca gaa ctg cac ctg gcc acc gaa gac cac aac gtg cca acc gaa     240
His Pro Glu Leu His Leu Ala Thr Glu Asp His Asn Val Pro Thr Glu
65                  70                  75                  80
```

-continued

| | |
|---|---|
| ggc atc aag act ggc tca ctg ctg gaa atc aac gac aag att tcc cgc<br>Gly Ile Lys Thr Gly Ser Leu Leu Glu Ile Asn Asp Lys Ile Ser Arg<br>                85                   90                  95 | 288 |
| ctg cag gta tct act ctg cgc gac aac tgt gaa gaa ttc ggc gtg cgc<br>Leu Gln Val Ser Thr Leu Arg Asp Asn Cys Glu Glu Phe Gly Val Arg<br>           100                    105                  110 | 336 |
| ctg cac cca atg ggt gat gtc cga cag ggc atc gtg cac acc gtc ggc<br>Leu His Pro Met Gly Asp Val Arg Gln Gly Ile Val His Thr Val Gly<br>        115                    120                  125 | 384 |
| cca cag ctc ggc gca acc cag cca ggc atg acc att gtg tgc ggt gac<br>Pro Gln Leu Gly Ala Thr Gln Pro Gly Met Thr Ile Val Cys Gly Asp<br>130                    135                  140 | 432 |
| tcc cac acc tcc acc cac ggt gct ttt ggc tcc atg gca ttc ggc atc<br>Ser His Thr Ser Thr His Gly Ala Phe Gly Ser Met Ala Phe Gly Ile<br>145                    150                  155                  160 | 480 |
| ggt acc tca gag gtt gag cac gtc atg gct act caa acc ctg cca ctg<br>Gly Thr Ser Glu Val Glu His Val Met Ala Thr Gln Thr Leu Pro Leu<br>                  165                  170                  175 | 528 |
| aag cct ttc aag acc atg gcc att gaa gtt act ggt gaa ctg cag cca<br>Lys Pro Phe Lys Thr Met Ala Ile Glu Val Thr Gly Glu Leu Gln Pro<br>        180                    185                  190 | 576 |
| ggt gtt tcc tcc aag gac ctg att ctg gcg att atc gcc aag atc ggc<br>Gly Val Ser Ser Lys Asp Leu Ile Leu Ala Ile Ile Ala Lys Ile Gly<br>            195                    200                  205 | 624 |
| acc ggc ggc gga cag ggc tac gtt ctg gaa tac cgc ggc gaa gca atc<br>Thr Gly Gly Gly Gln Gly Tyr Val Leu Glu Tyr Arg Gly Glu Ala Ile<br>        210                    215                  220 | 672 |
| cgt aag atg tcc atg gat gca cgc atg acc atg tgc aac atg tcc atc<br>Arg Lys Met Ser Met Asp Ala Arg Met Thr Met Cys Asn Met Ser Ile<br>225                    230                  235                  240 | 720 |
| gaa gct ggc gca cgt gcc ggc atg atc gcc cca gac caa acc acc ttc<br>Glu Ala Gly Ala Arg Ala Gly Met Ile Ala Pro Asp Gln Thr Thr Phe<br>                  245                  250                  255 | 768 |
| gac tac gtt gaa ggc cgc gaa atg gca cca aag ggc gcc gac tgg gac<br>Asp Tyr Val Glu Gly Arg Glu Met Ala Pro Lys Gly Ala Asp Trp Asp<br>        260                    265                  270 | 816 |
| gaa gca gtt gct tac tgg aag acc ctg cca acc gac gaa ggc gca acc<br>Glu Ala Val Ala Tyr Trp Lys Thr Leu Pro Thr Asp Glu Gly Ala Thr<br>            275                    280                  285 | 864 |
| ttt gac aag gtc gta gaa atc gat ggc tcc gca ctg acc cca ttc atc<br>Phe Asp Lys Val Val Glu Ile Asp Gly Ser Ala Leu Thr Pro Phe Ile<br>        290                    295                  300 | 912 |
| acc tgg ggc acc aac cca ggc cag ggc ctg cca ctg ggc gaa tcc gta<br>Thr Trp Gly Thr Asn Pro Gly Gln Gly Leu Pro Leu Gly Glu Ser Val<br>305                    310                  315                  320 | 960 |
| cca agc cca gaa gac ttc acc aac gac aac gac aag gca gca gcc gaa<br>Pro Ser Pro Glu Asp Phe Thr Asn Asp Asn Asp Lys Ala Ala Ala Glu<br>                  325                  330                  335 | 1008 |
| aag gca ctg cag tac atg gac ctg gta cca gga acc cca ctg cgc gac<br>Lys Ala Leu Gln Tyr Met Asp Leu Val Pro Gly Thr Pro Leu Arg Asp<br>        340                    345                  350 | 1056 |
| atc aag atc gac acc gtc ttc ctg gga tcc tgc acc aac gcc cgc atc<br>Ile Lys Ile Asp Thr Val Phe Leu Gly Ser Cys Thr Asn Ala Arg Ile<br>            355                    360                  365 | 1104 |
| gaa gac ctg cag atc gcc gct gac atc ctc aag ggc cac aaa atc gcc<br>Glu Asp Leu Gln Ile Ala Ala Asp Ile Leu Lys Gly His Lys Ile Ala<br>        370                    375                  380 | 1152 |

-continued

```
gac ggc atg cgc atg atg gtc gtg cct tcc tcc acc tgg atc aag caa    1200
Asp Gly Met Arg Met Met Val Val Pro Ser Ser Thr Trp Ile Lys Gln
385                 390                 395                 400 gag gca gaa gcg ctc gga ctg gac aaa atc ttc acc gac gct ggc gct    1248
Glu Ala Glu Ala Leu Gly Leu Asp Lys Ile Phe Thr Asp Ala Gly Ala
            405                 410                 415 gaa tgg cgt acc gca ggc tgc tcc atg tgc ctg ggc atg aac cca gac    1296
Glu Trp Arg Thr Ala Gly Cys Ser Met Cys Leu Gly Met Asn Pro Asp
        420                 425                 430 caa ctg aag cca ggc gag cgc tcc gca tcc acc tcc aac cga aac ttc    1344
Gln Leu Lys Pro Gly Glu Arg Ser Ala Ser Thr Ser Asn Arg Asn Phe
    435                 440                 445 gaa gga cgc caa gga cca gga ggc cgc acc cac ctg gta tcc cca gca    1392
Glu Gly Arg Gln Gly Pro Gly Gly Arg Thr His Leu Val Ser Pro Ala
450                 455                 460 gtc gca gcc gcc acc gca atc cgc ggc acc ctg tcc tca cct gca gat    1440
Val Ala Ala Ala Thr Ala Ile Arg Gly Thr Leu Ser Ser Pro Ala Asp
465                 470                 475                 480 atc                                                                 1443
Ile

<210> SEQ ID NO 4
<211> LENGTH: 591
<212> TYPE: DNA
<213> ORGANISM: Corynebacterium glutamicum ATCC13032

<400> SEQUENCE: 4 atg gaa aaa ttt acc acc tac acc ggc gtt ggc gtt cca ctg cag cga      48
Met Glu Lys Phe Thr Thr Tyr Thr Gly Val Gly Val Pro Leu Gln Arg
  1               5                  10                  15 tcc aac gtg gac acc gac cag atc atc cca gcc gtc tac ctc aag cgc      96
Ser Asn Val Asp Thr Asp Gln Ile Ile Pro Ala Val Tyr Leu Lys Arg
             20                  25                  30 gtc acc cgg acc ggc ttc gaa gac gga ctg ttt tcc aac tgg cgc caa     144
Val Thr Arg Thr Gly Phe Glu Asp Gly Leu Phe Ser Asn Trp Arg Gln
         35                  40                  45 aac gac ccc aac ttt gtc ctc aac acc gac acc tac aag aac ggc tcc     192
Asn Asp Pro Asn Phe Val Leu Asn Thr Asp Thr Tyr Lys Asn Gly Ser
     50                  55                  60 gtt ctc gta gca ggc cct gac ttt ggc acc ggc tcc tcc cgc gag cac     240
Val Leu Val Ala Gly Pro Asp Phe Gly Thr Gly Ser Ser Arg Glu His
 65                  70                  75                  80 gcc gtc tgg gca ctc atg gac tac ggc ttc cgc gct gtc ttc tcc tca     288
Ala Val Trp Ala Leu Met Asp Tyr Gly Phe Arg Ala Val Phe Ser Ser
                 85                  90                  95 cga ttc gcc gac atc ttc cgc ggc aac tcc gga aaa gcg ggc atg ctc     336
Arg Phe Ala Asp Ile Phe Arg Gly Asn Ser Gly Lys Ala Gly Met Leu
            100                 105                 110 acc ggc atc atg gaa cag tcc gac atc gaa ctt ctg tgg aag ctc atg     384
Thr Gly Ile Met Glu Gln Ser Asp Ile Glu Leu Leu Trp Lys Leu Met
        115                 120                 125 gaa caa acc cca ggc ctc gaa ctg acc gtg aac ctg gaa aag cag atc     432
Glu Gln Thr Pro Gly Leu Glu Leu Thr Val Asn Leu Glu Lys Gln Ile
    130                 135                 140 gtc acc gca ggc gac gta gtg atc agc ttc gaa gtt gac ccc tac atc     480
Val Thr Ala Gly Asp Val Val Ile Ser Phe Glu Val Asp Pro Tyr Ile
145                 150                 155                 160 cgc tgg cgt ttg atg gaa ggc ctc gac gac gct ggc ctg acc ctg cgc     528
Arg Trp Arg Leu Met Glu Gly Leu Asp Asp Ala Gly Leu Thr Leu Arg
```

```
                Arg Trp Arg Leu Met Glu Gly Leu Asp Asp Ala Gly Leu Thr Leu Arg
                                165                 170                 175 aag ctc gat gaa att gaa gac tac gag gct aag cgc cct gcg ttt aag                     576
Lys Leu Asp Glu Ile Glu Asp Tyr Glu Ala Lys Arg Pro Ala Phe Lys
            180                 185                 190 cca cgc act aac gct                                                                 591
Pro Arg Thr Asn Ala
        195

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 5
ccaggagacc gcacccacct g                                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 6
caggtgggtg cggtctcctg g                                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 7
atgaccagcc ccgtggagaa c                                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 8
ttaagcgtta gtgcgtggct t                                                              21
```

MUTANT ISOPROPYLMALATE ISOMERASE

This application is the US national phase of international application PCT/JP03/03353 filed 19 Mar. 2003, which designated the US and claims benefit of JP Application No. 2002-076228 filed 19 Mar. 2002, the entire contents of each of which are incorporated herein by reference.

TECHNICAL FIELD

The present invention relates to a novel polypeptide, a DNA encoding the polypeptide, a recombinant DNA comprising the DNA, a microorganism transformed with the recombinant DNA, a microorganism comprising the DNA on its chromosomal DNA, and a process for producing an L-amino acid which comprises culturing the microorganism in a medium.

BACKGROUND OF THE INVENTION

Isopropylmalate isomerase is an enzyme which catalyzes a reaction on the leucine synthesis pathway to convert 2-isopropylmalic acid to 3-isopropylmalic acid.

Also, an isopropylmalate isomerase large subunit (hereinafter referred to as "ISOM") is a polypeptide which forms a complex with an isopropylmalate isomerase small subunit to constitute isopropylmalate isomerase.

In recent years, complete genomic sequences have been decoded in various microorganisms such as *Escherichia coli* and *Bacillus subtilis* [*Science*, 277, 1453 (1997), *Nature*, 390, 249 (1997)], and the nucleotide sequence of a DNA encoding ISOM has also been found.

In microorganisms belonging to the genus *Corynebacterium*, a gene encoding ISOM was predicted from genomic sequence information in *Corynebacterium glutamicum* and its nucleotide sequence has been reported (WO 01/00843, EP 1108790).

On the other hand, an ISOM-deficient leucine-requiring mutant has been obtained from a lysine-producing strain of *Corynebacterium glutamicum* [*Appl. Microbiol. Biotechnol.*, 37, 566 (1992)]. It has been reported in this reference that when this leucine-requiring mutant is cultured in a medium supplemented with a certain concentration of leucine, its growth level is appropriately inhibited, and lysine accumulation increases.

Furthermore, correlation between leucine requirement and lysine production has been examined by using a lysine-producing strain of *Corynebacterium glutamicum* from which isopropylmalic acid synthase as another enzyme on the leucine synthesis pathway was deficient, and it has been reported that inhibition of the growth level is the highest possibility of the reason for the increase of the lysine accumulation when the added amount of leucine to the medium during the cultivation is limited [*Appl. Environ. Microbiol.*, 60, 133 (1994)].

However, it is not known so far that productivity of L-lysine can be improved by introducing a mutation in the DNA encoding ISOM, without adding leucine to a production medium and without causing significant change in the growth level. In addition, there are no reports describing and suggesting that productivity of not only L-lysine but other many L-amino acids can also be improved by a mutation of ISOM and that introduction of what type of mutation into the DNA encoding ISOM can bring the above-described effect.

DISCLOSURE OF THE INVENTION

An object of the present invention is to provide a process for efficiently producing an L-amino acid by using a microorganism.

The present inventors found that a microorganism capable of expressing a mutant isopropylmalate isomerase of the present invention exhibits a significantly high L-amino acid productivity without adding leucine to a medium, in comparison with microorganisms expressing a wild type isopropylmalate isomerase, and thus the present invention has been completed.

The present invention relates to the following (1) to (28).

(1) A polypeptide comprising an amino acid sequence in which at least one amino acid is deleted, substituted or added in an amino acid sequence of isopropylmalate isomerase derived from a microorganism belonging to coryneform bacteria, wherein a coryneform bacterium which produces the polypeptide comprising the amino acid sequence as the sole isopropylmalate isomerase exhibits a partial leucine requirement in a minimal medium.

(2) The polypeptide according to (1), which comprises an amino acid sequence in which at least one amino acid is deleted, substituted or added in the amino acid sequence of an isopropylmalate isomerase large subunit (hereinafter referred to as "ISOM") constituting the isopropylmalate isomerase.

A polypeptide comprising an amino acid sequence in which at least one amino acid is deleted, substituted or added in an amino acid sequence of ISOM derived from a microorganism belonging to coryneform bacteria, wherein a coryneform bacterium which produces the polypeptide comprising the amino acid sequence as the sole ISOM exhibits a partial leucine requirement in a minimal medium.

(4) A polypeptide comprising an amino acid sequence in which an amino acid residue at a position corresponding to the amino acid at position 456 from the N-terminal of the amino acid sequence represented by SEQ ID NO:1 in an amino acid sequence of ISOM derived from a microorganism belonging to coryneform bacteria is an amino acid residue other than a glycine residue.

(5) The polypeptide according to (4), wherein the amino acid residue other than a glycine residue is an amino acid residue selected from the group consisting of L-alanine, L-valine, L-leucine, L-isoleucine, L-methionine, L-tryptophan, L-phenylalanine, L-proline, L-lysine, L-histidine, L-arginine, L-aspartic acid and L-glutamic acid.

(6) The polypeptide according to (4), wherein the amino acid residue other than a glycine residue is L-aspartic acid or L-glutamic acid.

(7) The polypeptide according to any one of (1) to (6), wherein the microorganism belonging to coryneform bacteria is a microorganism belonging to the genus *Corynebacterium*, the genus *Brevibacterium* or the genus *Mycobacterium*.

(8) A polypeptide comprising an amino acid sequence in which an amino acid residue at position 456 from the N-terminal of the amino acid sequence represented by SEQ ID NO:1 is substituted with an amino acid residue other than a glycine residue.

(9) The polypeptide according to (8), wherein the amino acid residue other than a glycine residue is an amino acid residue selected from the group consisting of L-alanine, L-valine, L-leucine, L-isoleucine, L-methionine, L-tryptophan, L-phenylalanine, L-proline, L-lysine, L-histidine, L-arginine, L-aspartic acid and L-glutamic acid.

(10) The polypeptide according to (8), wherein the amino acid residue other than a glycine residue is L-aspartic acid or L-glutamic acid.

(11) A polypeptide comprising an amino acid sequence in which at least one amino acid other than an amino acid residue at a position corresponding to the amino acid at position 456 from the N-terminal of the amino acid sequence represented by SEQ ID NO:1 in the amino acid sequence of the polypeptide according to any one of (4) to (10) is deleted or substituted, wherein a coryneform bacterium which produces the polypeptide comprising the amino acid sequence as the sole ISOM exhibits a partial leucine requirement in a minimal medium.

(12) A polypeptide comprising an amino acid sequence in which at least one amino acid is added in the amino acid sequence of the polypeptide according to any one of (4) to (11), wherein a coryneform bacterium which produces the polypeptide comprising the amino acid sequence as the sole ISOM exhibits a partial leucine requirement in a minimal medium.

(13) A DNA encoding the polypeptide according to any one of (1) to (12).

(14) A DNA comprising a nucleotide sequence in which a region corresponding to the nucleotide sequence of positions 1,366 to 1,368 from the 5'-terminal of the nucleotide sequence represented by SEQ ID NO:3 in the nucleotide sequence of a DNA encoding ISOM derived from a microorganism belonging to coryneform bacteria is a codon encoding an amino acid residue other than a glycine residue.

(15) The DNA according to (14), wherein the codon encoding an amino acid residue other than a glycine residue is a codon encoding an amino acid residue selected from the group consisting of L-alanine, L-valine, L-leucine, L-isoleucine, L-methionine, L-tryptophan, L-phenylalanine, L-proline, L-lysine, L-histidine, L-arginine, L-aspartic acid and L-glutamic acid.

(16) The DNA according to (14), wherein the codon encoding an amino acid residue other than a glycine residue is a codon encoding L-aspartic acid or L-glutamic acid.

(17) The DNA according to any one of (14) to (16), wherein the microorganism belonging to coryneform bacteria is a microorganism belonging to the genus *Corynebacterium*, the genus *Brevibacterium* or the genus *Mycobacterium*.

(18) A DNA comprising a nucleotide sequence in which a nucleotide sequence of positions 1,366 to 1,368 from the 5'-terminal of the nucleotide sequence represented by SEQ ID NO:3 is a codon encoding an amino acid residue other than a glycine residue.

(19) The DNA according to (18), wherein the codon encoding an amino acid residue other than a glycine residue is a codon encoding an amino acid residue selected from the group consisting of L-alanine, L-valine, L-leucine, L-isoleucine, L-methionine, L-tryptophan, L-phenylalanine, L-proline, L-lysine, L-histidine, L-arginine, L-aspartic acid and L-glutamic acid.

(20) The DNA according to (18), wherein the codon encoding an amino acid residue other than a glycine residue is a codon encoding L-aspartic acid or L-glutamic acid.

(21) A DNA which hybridizes with a DNA consisting of a nucleotide sequence complementary to the nucleotide sequence represented by SEQ ID NO:3 under stringent conditions and comprises a nucleotide sequence in which a region corresponding to the nucleotide sequence of positions 1,366 to 1,368 from the 5'-terminal of the nucleotide sequence represented by SEQ ID NO:3 is a codon encoding an amino acid residue other than a glycine residue, wherein a coryneform bacterium which produces the polypeptide encoded by the DNA as the sole ISOM exhibits a partial leucine requirement in a minimal medium.

(22) A recombinant DNA which comprises the DNA according to any one of (13) to (21).

(23) A microorganism transformed with the recombinant DNA according to (22).

(24) A microorganism which comprises the DNA according to any one of (13) to (21) on its chromosomal DNA.

(25) The microorganism according to (23) or (24), which is a microorganism belonging to the genus *Corynebacterium*, the genus *Brevibacterium* or the genus *Microbacterium*.

(26) The microorganism according to (25), wherein the microorganism belonging to the genus *Corynebacterium* is *Corynebacterium glutamicum*.

(27) A process for producing an L-amino acid, which comprises culturing the microorganism according to any one of (23) to (26) in a medium to produce and accumulate the L-amino acid in the culture, and recovering the L-amino acid from the culture.

(28) The process according to (27), wherein the L-amino acid is an amino acid selected from the group consisting of L-lysine, L-threonine, L-glutamine, L-arginine, L-proline and L-tryptophan.

[1] Polypeptide of the Present Invention

The polypeptide of the present invention includes:

(i) a polypeptide comprising an amino acid sequence in which at least one amino acid is deleted, substituted or added in an amino acid sequence of isopropylmalate isomerase derived from a microorganism belonging to coryneform bacteria, wherein a coryneform bacterium which produces the polypeptide comprising the amino acid sequence as the sole isopropylmalate isomerase exhibits a partial leucine requirement in a minimal medium;

(ii) the polypeptide according to (i), which comprises an amino acid sequence in which at least one amino acid is deleted, substituted or added in the amino acid sequence of an isopropylmalate isomerase large subunit (hereinafter referred to as "ISOM") constituting the isopropylmalate isomerase;

(iii) a polypeptide comprising an amino acid sequence in which at least one amino acid is deleted, substituted or added in an amino acid sequence of ISOM derived from a microorganism belonging to coryneform bacteria, wherein a coryneform bacterium which produces the polypeptide comprising the amino acid sequence as the sole ISOM exhibits a partial leucine requirement in a minimal medium;

(iv) a polypeptide comprising an amino acid sequence in which an amino acid residue at a position corresponding to the amino acid at position 456 from the N-terminal of the amino acid sequence represented by SEQ ID NO:1 in an amino acid sequence of ISOM derived from a microorganism belonging to coryneform bacteria is an amino acid residue other than a glycine residue;

(v) the polypeptide according to (iv), wherein the amino acid residue other than a glycine residue is an amino acid residue selected from the group consisting of L-alanine, L-valine, L-leucine, L-isoleucine, L-methionine, L-tryptophan, L-phenylalanine, L-proline, L-lysine, L-histidine, L-arginine, L-aspartic acid and L-glutamic acid;

(vi) the polypeptide according to (iv), wherein the amino acid residue other than a glycine residue is L-aspartic acid or L-glutamic acid;

(vii) the polypeptide according to any one of (i) to (vi), wherein the microorganism belonging to coryneform bacteria is a microorganism belonging to the genus *Corynebacterium*, the genus *Brevibacterium* or the genus *Mycobacterium*;

(viii) a polypeptide comprising an amino acid sequence in which an amino acid residue at position 456 from the N-terminal of the amino acid sequence represented by SEQ ID NO:1 is substituted with an amino acid residue other than a glycine residue;

(ix) the polypeptide according to (viii), wherein the amino acid residue other than a glycine residue is an amino acid residue selected from the group consisting of L-alanine, L-valine, L-leucine, L-isoleucine, L-methionine, L-tryptophan, L-phenylalanine, L-proline, L-lysine, L-histidine, L-arginine, L-aspartic acid and L-glutamic acid;

(x) the polypeptide according to (viii), wherein the amino acid residue other than a glycine residue is L-aspartic acid or L-glutamic acid;

(xi) a polypeptide comprising an amino acid sequence in which at least one amino, acid other than an amino acid residue at a position corresponding to the amino acid at position 456 from the N-terminal of the amino acid sequence represented by SEQ ID NO:1 in the amino acid sequence of the polypeptide according to any one of (iv) to (x) is deleted or substituted, wherein a coryneform bacterium which produces the polypeptide comprising the amino acid sequence as the sole ISOM exhibits a partial leucine requirement in a minimal medium; and (xii) a polypeptide comprising an amino acid sequence in which at least one amino acid is added in the amino acid sequence of the polypeptide according to any one of (iv) to (xi), wherein a coryneform bacterium which produces the polypeptide comprising the amino acid sequence as the sole ISOM exhibits a partial leucine requirement in a minimal medium.

The isopropylmalate isomerase derived from a microorganism belonging to coryneform bacteria includes isopropylmalate isomerases derived from a microorganism belonging to the genus *Corynebacterium*, the genus *Brevibacterium* or the genus *Microbacterium*, which is a microorganism belonging to coryneform bacteria defined in *Bergey's Manual of Determinative Bacteriology*, 8, 599 (1974), such as isopropylmalate isomerases derived from microorganisms such as *Corynebacterium acetoacidophilum*, *Corynebacterium acetoglutamicum*, *Corynebacterium callunae*, *Corynebacterium glutamicum*, *Corynebacterium herculis*, *Corynebacterium lilium*, *Corynebacterium melassecola*, *Corynebacterium thermoaminogenes*, *Brevibacterium saccharolyticum*, *Brevibacterium immariophilum*, *Brevibacterium roseum*, *Brevibacterium thiogenitalis*, and *Microbacterium ammoniaphilum*.

The above-described isopropylmalate isomerase derived from a microorganism belonging to coryneform bacteria can be obtained by hybridization described below using, as a probe, a complementary chain of a DNA comprising the nucleotide sequence represented by SEQ ID NO:3 or SEQ ID NO:4 or a complementary chain of a DNA comprising a part of the DNA, or by a usual method using an isopropylmalate isomerase-encoding DNA, wherein said isopropylmalate isomerase-encoding DNA can be obtained by PCR using a primer DNA designed from the nucleotide sequence represented by SEQ ID NO:3 or SEQ ID NO:4 and the above-described coryneform bacterial chromosomal DNA as the template.

The isopropylmalate isomerase derived from a microorganism belonging to coryneform bacteria includes the isopropylmalate isomerase constituted by a polypeptide consisting of the amino acid sequence represented by SEQ ID NO:1 or SEQ ID NO:2 as described in EP 1108790.

The polypeptide comprising an amino acid sequence in which at least one amino acid is deleted, substituted or added in an amino acid sequence of isopropylmalate isomerase derived from a microorganism belonging to coryneform bacteria includes a polypeptide comprising an amino acid sequence in which at least one amino acid in both or either of the amino acid sequences of an isopropylmalate isomerase small subunit and an isopropylmalate isomerase large subunit (ISOM) is deleted, substituted or added, and preferred is a polypeptide comprising an amino acid sequence in which at least one amino acid in the amino acid sequence of ISOM is deleted, substituted or added.

The subunit comprising an amino acid sequence in which at least one amino acid in both or either of the amino acid sequences of the small subunit and ISOM of the isopropylmalate isomerase derived from a microorganism belonging to coryneform bacteria is deleted, substituted or added can be obtained by introducing a site-directed mutation into both or either of the DNAs encoding the small subunit and ISOM, e.g., into both or either of the DNAs encoding the amino acid sequences represented by SEQ ID NO:1 and SEQ ID NO:2, by using the site-directed mutagenesis described in *Molecular Cloning, A Laboratory Manual*, Third Edition, Cold Spring Harbor Laboratory Press (2001) (hereinafter referred to as "*Molecular Cloning*, Third Edition"), *Current Protocols in Molecular Biology*, John Wiley & Sons (1987-1997) (hereinafter referred to as "*Current Protocols in Molecular Biology*"), *Nucleic Acids Research*, 10, 6487 (1982), *Proc. Natl. Acad. Sci. USA*, 79, 6409 (1982), *Gene*, 34, 315 (1985), *Nucleic Acids Research*, 13, 4431 (1985), *Proc. Natl. Acad. Sci. USA*, 82, 488 (1985) or the like.

The number of the amino acids which are deleted, substituted or added is not particularly limited; however, it is such a number that deletion, substitution or addition can be carried out by a known method such as a method for introducing a site-directed mutation. The number is 1 to several tens, preferably 1 to 20, more preferably 1 to 10, and most preferably 1 to 5.

Also, the deletion, substitution or addition of at least one amino acid residue means that one or at least two amino acids are deleted, substituted or added at any position in the same sequence. The deletion, substitution or addition can occur in the same amino acid sequence simultaneously. The amino acid residue to be substituted or added can be natural or non-natural, and natural one is preferred. The natural amino acid residue includes L-alanine, L-asparagine, L-aspartic acid, L-glutamine, L-glutamic acid, glycine, L-histidine, L-isoleucine, L-leucine, L-lysine, L-methionine; L-phenylalanine, L-proline, L-serine, L-threonine, L-tryptophan, L-tyrosine, L-valine, L-cysteine, and the like.

Herein, examples of amino acid residues which are substituted with each other are shown below. Amino acid residues in the same group can be substituted with each other.

Group A:
leucine, isoleucine, norleucine, valine, norvaline, alanine, 2-aminobutanoic acid, methionine, O-methylserine, t-butylglycine, t-butylalanine, cyclohexylalanine;

Group B:
asparatic acid, glutamic acid, isoasparatic acid, isoglutamic acid, 2-aminoadipic acid, 2-aminosuberic acid;

Group C:
asparagine, glutamine;

Group D:
  lysine, arginine, ornithine, 2,4-diaminobutanoic acid, 2,3-diaminopropionic acid;

Group E:
  proline, 3-hydroxyproline, 4-hydroxyproline;

Group F:
  serine, threonine, homoserine;

Group G:
  phenylalanine, tyrosine.

In order that the polypeptide of the present invention in the above [1] has activity as isopropylmaclic acid isomerase, it has a homology of at least 60% or more, generally 80% or more, and particularly 95% or more, with the amino acid sequence represented by SEQ ID NO:1 or 2.

The homology of an amino acid sequence or a nucleotide sequence can be determined, for example, by using the algorithm BLAST by Karlin and Altschl [Proc. Natl. Acad. Sci. USA, 90, 5873 (1993)] or FASTA [Methods Enzymol., 183, 63 (1990)]. The programs called BLASTN and BLASTX have developed based on the algorithm BLAST [J. Mol. Biol, 215, 403 (1990)]. In the case of analyzing a nucleotide sequence by BLASTN based on BLAST, for example, the parameter can be set to score=100, wordlength=12. Also, in the case of analyzing an amino acid sequence by BLASTX based on BLAST, for example, the parameter can be set to score=50, wordlength=3. When BLAST and Gapped BLAST programs are used, a default parameter of each program can be used. The specific analysis methods using the above programs are known (URL http://www.ncbi.nlm.nih.gov/.).

The coryneform bacterium which produces a polypeptide comprising an amino acid sequence in which at least one amino acid in the amino acid sequence of the isopropylmalate isomerase derived from a microorganism belonging to coryneform bacteria is deleted, substituted or added as the sole isopropylmalate isomerase can be obtained by transforming a coryneform bacterium capable of producing a wild type isopropylmalate isomerase by using a DNA encoding the polypeptide which can be obtained by the above-described method, and replacing a DNA encoding the wild type isopropylmalate isomerase with the DNA encoding the polypeptide which can be obtained by the above-described method by a homologous recombination technique.

"The coryneform bacterium which produces a polypeptide comprising an amino acid sequence in which one or more of amino acids in the amino acid sequence of the isopropylmalate isomerase derived from a microorganism belonging to coryneform bacteria are deleted, substituted or added as the sole isopropylmalate isomerase exhibits a partial leucine requirement in a minimal medium" means that, when the coryneform bacterium is cultured in a minimal medium, its growth can be recognized but the growth rate is slower than the growth rate of the wild type isopropylmalate isomerase-producing coryneform bacterium when it is grown in the minimal medium, and the growth rate is recovered by adding an appropriate amount of leucine.

In the present specification, "the wild type isopropylmalate isomerase" means an isopropylmalate isomerase in a microorganism belonging to coryneform bacteria which does not exhibit leucine requirement when cultured in a minimal medium, preferably an isopropylmalate isomerase in a wild type strain which does not exhibit leucine requirement. "The wild type strain" means a type of a microorganism which can be most frequently found in the natural population among species to which the microorganism belongs. The wild type strain of a microorganism belonging to coryneform bacteria includes *Corynebacterium acetoacidophilum* ATCC13870, *Corynebacterium acetoglutamicum* ATCC15806, *Corynebacterium callunae* ATCC15991, *Corynebacterium glutamicum* ATCC13032, *Corynebacterium glutamicum* ATCC13060, *Corynebacterium glutamicum* ATCC13826 (prior genus and species: *Brevibacterium flavum* or *Corynebacterium lactofermentum*), *Corynebacterium glutamicum* ATCC14020 (prior genus and species: *Brevibacterium divaricatum*), *Corynebacterium glutamicum* ATCC13869 (prior genus and species: *Brevibacterium lactofermentum*), *Corynebacterium herculis* ATCC13868, *Corynebacterium lilium* ATCC15990, *Corynebacterium melassecola* ATCC17965, *Corynebacterium thermoaminogenes* ATCC9244, *Brevibacterium saccharolyticum* ATCC14066, *Brevibacterium immariophilum* ATCC14068, *Brevibacterium roseum* ATCC13825, *Brevibacterium thiogenitalis* ATCC19240, *Microbacterium ammoniaphilum* ATCC15354, and the like.

In the present specification, when the microorganism belonging to coryneform bacteria is a strain which exhibits auxotrophic, the minimal medium includes a medium to which the auxotrophic substance is added. However, leucine is not included in the auxotrophic substance.

The above-described exhibition of partial leucine requirement specifically means that a mutant strain, which is obtained by transforming a wild strain of *Corynebacterium glutamicum* ATCC13032 with a DNA encoding a polypeptide having an amino acid sequence in which at least one of amino acids in the amino acid sequence of the isopropylmalate isomerase derived from a microorganism belonging to coryneform bacteria is deleted, substituted or added, and then by substituting the DNA with a DNA encoding the wild type isopropylmalate isomerase by a homologous recombination technique, exhibits the following property.

That is, when each of the mutant strain and wild strain ATCC13032 is spread on a minimal agar medium [1% glucose, 0.4% ammonium chloride, 0.2% urea, 0.1% potassium dihydrogenphosphate, 0.3% dipotassium hydrogenphosphate, 0.04% magnesium sulfate, 10 mg/L iron sulfate, 1 mg/L manganese sulfate, 5 mg/L nicotinic acid, 100 µg/L biotin, 5 mg/L thiamine hydrochloride, 1.6% bacto agar (Difco), pH 7.2] to give a density of 1 to 10 cells/cm² and cultured at 30° C. for 2 to 3 days, the mutant strain forms a colony having a colony diameter of 90% or less, preferably 80% or less, more preferably 70% or less, and most preferably 50% or less, of the colony of ATCC13032, and can be fully recognized with the naked eye (colony diameter: 0.1 mm or more). When the mutant is spread on the minimal medium supplemented with 50 mg/L of leucine and cultured at 30° C. for 2 to 3 days in the same manner, it forms a colony having a size identical to that of ATCC13032.

A coryneform bacterium, which produces as the sole isopropylmalate isomerase the polypeptide of the present invention having the above-described property and described in the above item (i), shows equivalent growth to that of a coryneform bacterium which produces a wild type isopropylmalate isomerase in a usual production medium to be used in an amino acid fermentation without adding leucine. Although the composition of the production medium varies depending on the amino acid to be produced, a medium prepared by adding nutrient sources such as vitamins and inexpensive natural materials such as corn steep liquor and soybean hydrolysate as the nitrogen source to a minimal medium is generally used in the amino acid fermentation for the purpose of accelerating growth of the strain. Since leucine is contained in the natural materials in a trace amount, the partial leucine requirement of the coryneform bacterium which produces the polypeptide of the present invention described in the above item (i) as the sole isopropylmalate isomerase is complemented.

Since the polypeptide of the present invention described in the above item (ii) is a polypeptide having a mutation in ISOM of the polypeptide of the present invention described in the above item (i), it can be obtained by a method similar to the above.

The polypeptide of the present invention described in the above item (iii) can be obtained by a method similar to that in the above-described item (i).

That is, a DNA encoding a polypeptide comprising an amino acid sequence in which at least one amino acid in the amino acid sequence of ISOM derived from a microorganism belonging to coryneform bacteria is deleted, substituted or added can be obtained by introducing a mutation into a DNA encoding ISOM derived from a microorganism belonging to coryneform bacteria by the above-described site-directed mutagenesis.

Whether the polypeptide obtained by the above-described method is the polypeptide of the present invention described in the above item (iii) can be confirmed by examining whether a coryneform bacterium obtained by transforming a coryneform bacterium capable of producing a wild type ISOM with a DNA encoding the polypeptide, and substituting the DNA with a DNA encoding the wild type ISOM by a homologous recombination technique exhibits the above-described partial leucine requirement in a minimal medium.

As to the polypeptide of the present invention described in the above item (iv), "the amino acid residue at a position corresponding to the amino acid at position 456 from the N-terminal of the amino acid sequence represented by SEQ ID NO:1 in ISOM derived from a microorganism belonging to coryneform bacteria" means an amino acid residue at a position corresponding to the amino acid at position 456 from the N-terminal of the amino acid sequence represented by SEQ ID NO:1 in the amino acid sequence in ISOM derived from the coryneform bacterium when homology of the amino acid sequence in ISOM derived from the coryneform bacterium with the amino acid sequence represented by SEQ ID NO:1 is calculated by using a homology analyzing program such as the above-described BLAST or FASTA, and the amino acid sequences are aligned such that the homology between both amino acid sequences becomes highest.

As the amino acid residue other than a glycine residue, any amino acid can be used, so long as it is an amino acid residue other than a glycine residue, and is preferably an amino acid residue selected from the group consisting of L-alanine, L-valine, L-leucine, L-isoleucine, L-methionine, L-tryptophan, L-phenylalanine, L-proline, L-lysine, L-histidine, L-arginine, L-aspartic acid and L-glutamic acid residues, more preferably an L-aspartic acid or L-glutamic acid residues, and most preferably an L-aspartic acid residue.

Each of the polypeptides described in the above items (iv) to (vii) can be obtained by using a DNA in which the codon encoding an amino acid residue corresponding to the glycine residue at position 456 from the N-terminal of the amino acid sequence represented by SEQ ID NO:1 in the DNA encoding ISOM derived from a microorganism belonging to coryneform bacteria is changed to a codon encoding an amino acid residue other than a glycine residue by using the above-described site-directed mutagenesis.

Whether the mutant DNA is the DNA encoding the polypeptide of the present invention described in the above item (iv) can be confirmed by examining whether a transformant obtained by transforming a coryneform bacterium capable of producing a wild type ISOM with the mutant DNA, and substituting the mutant DNA with a DNA encoding the wild type ISOM by a homologous recombination technique exhibits the above-described partial leucine requirement.

Each of the polypeptides of the present invention in the above-described items (viii) to (x) can be obtained by changing the codon encoding a glycine residue at position 456 from the N-terminal of the amino acid sequence represented by SEQ ID NO:1 to a codon encoding an amino acid residue other than a glycine residue by the above-described site-directed mutagenesis.

The amino acid residue other than a glycine residue is preferably an amino acid residue selected from the group consisting of L-alanine, L-valine, L-leucine, L-isoleucine, L-methionine, L-tryptophan, L-phenylalanine, L-proline, L-lysine, L-histidine, L-arginine, L-aspartic acid and L-glutamic acid residues, more preferably an L-aspartic acid or L-glutamic acid residue, and more preferably an L-aspartic acid residue.

The polypeptide described in the above item (x) can be obtained by applying the above-described site-directed mutagenesis to a DNA encoding the polypeptide of the present invention described in any one of the above-described items (iv) to (ix). The site-directed mutation to be introduced may be any mutation, so long as, in the polypeptide of the present invention described in any one of the above-described items (iv) to (ix), an amino acid residue(s) other than an amino acid residue corresponding to the amino acid at position 456 from the N-terminal of the amino acid sequence represented by SEQ ID NO:1 is/are deleted or substituted.

Furthermore, the polypeptide in the above-described item (x) can also be obtained by deleting or substituting an amino acid residue(s) other than an amino acid residue corresponding to the amino acid at position 456 from the N-terminal of the amino acid sequence represented by SEQ ID NO:1 according to the above-described site-directed mutagenesis at the time when the polypeptide of the present invention described in any one of the above-described items (iv) to (ix) is obtained.

The amino acid residue to be deleted or substituted is not particularly limited, so long as it is an amino acid residue other than an amino acid residue corresponding to the amino acid at position 456 from the N-terminal of the amino acid sequence represented by SEQ ID NO:1.

Whether the polypeptide obtained in the above is the polypeptide of the present invention described in the above item (x) can be confirmed by examining whether a coryneform bacterium obtained by transforming a coryneform bacterium capable of producing a wild type ISOM with a DNA encoding the polypeptide, and substituting the DNA with a DNA encoding the wild type ISOM by a homologous recombination technique exhibits the above-described partial leucine requirement.

The polypeptide in the above-described item (xi) can be obtained by applying the above-described site-directed mutagenesis to a DNA encoding the polypeptide of the present invention described in any one of the above-described items (iv) to (x).

Furthermore, it can also be obtained by adding an amino acid residue(s) to the amino acid sequence represented by SEQ ID NO:1 according to the above-described site-directed mutagenesis at the time when the polypeptide of the present invention described in any one of the above-described items (iv) to (x) is obtained.

Whether the polypeptide obtained in the above is the polypeptide of the present invention described in the above item (xi) can be confirmed by examining whether a coryneform bacterium obtained by transforming a coryneform bacterium capable of producing a wild type ISOM with a DNA encoding the polypeptide, and substituting the DNA with a DNA encoding the wild type ISOM by a homologous recombination technique exhibits the above-described partial leucine requirement.

The number of the amino acids which are deleted, substituted or added is not particularly limited; however, it is such a number that deletion, substitution or addition can be carried out by a known method such as a method for introducing a site-directed mutation. The number is 1 to several tens, preferably 1 to 20, more preferably 1 to 10, and most preferably 1 to 5.

"The deletion, substitution or addition of at least one amino acid residue" means that one or at least two amino acids are deleted, substituted or added at any position in the same sequence, the deletion, substitution or addition can be carried out in the same amino acid sequence simultaneously, the amino acid residue substituted or added can be natural or non-natural, and the amino acids to be substituted are the same as those described above.

In order that the polypeptides in the above-described items (x) or (xi) have activity as ISOM, it is preferred that homology with the amino acid sequence represented by SEQ ID NO:1 is at least 60% or more, generally 80% or more, and particularly preferably 95% or more, when calculated by using the above-described BLAST, FASTA or the like based on the above-described parameters.

[2] DNA of the Present Invention

The DNA of the present invention includes:
(i) a DNA encoding the above-described polypeptide of the present invention,
(ii) a DNA comprising a nucleotide sequence in which a region corresponding to the nucleotide sequence of positions 1,366 to 1,368 from the 5'-terminal of the nucleotide sequence represented by SEQ ID NO:3 in the nucleotide sequence of a DNA encoding ISOM derived from a microorganism belonging to coryneform bacteria is a codon encoding an amino acid residue other than a glycine residue;
(iii) the DNA according to (ii), wherein the codon encoding an amino acid residue other than a glycine residue is a codon encoding an amino acid residue selected from the group consisting of L-alanine, L-valine, L-leucine, L-isoleucine, L-methionine, L-tryptophan, L-phenylalanine, L-proline, L-lysine, L-histidine, L-arginine, L-aspartic acid and L-glutamic acid;
(iv) the DNA according to (ii), wherein the codon encoding an amino acid residue other than a glycine residue is a codon encoding L-aspartic acid or L-glutamic acid;
(v) the DNA according to any one of (ii) to (iv), wherein the microorganism belonging to coryneform bacteria is a microorganism belonging to the genus *Corynebacterium*, the genus *Brevibacterium* or the genus *Mycobacterium*;
(vi) a DNA comprising a nucleotide sequence in which a nucleotide sequence of positions 1,366 to 1,368 from the 5'-terminal of the nucleotide sequence represented by SEQ ID NO:3 is a codon encoding an amino acid residue other than a glycine residue;
(vii) the DNA according to (vi), wherein the codon encoding an amino acid residue other than a glycine residue is a codon encoding an amino acid residue selected from the group consisting of L-alanine, L-valine, L-leucine, L-isoleucine, L-methionine, L-tryptophan, L-phenylalanine, L-proline, L-lysine, L-histidine, L-arginine, L-aspartic acid and L-glutamic acid;
(viii) the DNA according to (vi), wherein the codon encoding an amino acid residue other than a glycine residue is a codon encoding L-aspartic acid or L-glutamic acid; and
(ix) a DNA which hybridizes with a DNA consisting of a nucleotide sequence complementary to the nucleotide sequence represented by SEQ ID NO:3 under stringent conditions and comprises a nucleotide sequence in which a region corresponding to the nucleotide sequence of positions 1,366 to 1,368 from the 5'-terminal of the nucleotide sequence represented by SEQ ID NO:3 is a codon encoding an amino acid residue other than a glycine residue, wherein a coryneform bacterium which produces the polypeptide encoded by the DNA as the sole ISOM exhibits a partial leucine requirement in a minimal medium.

In the DNA of the present invention described in the above item (ii), as the DNA encoding ISOM derived from a microorganism belonging to coryneform bacteria, mentioned is a DNA encoding ISOM of isopropylmalate isomerase derived from a microorganism belonging to coryneform bacteria described in the above-described [1].

The DNA encoding ISOM derived from a microorganism belonging to coryneform bacteria may be any DNA, so long as it is a DNA encoding ISOM of isopropylmalate isomerase derived from a microorganism belonging to coryneform bacteria described in the above-described [1].

The DNA can be obtained by the method of the above-described [1].

The DNA encoding ISOM derived from a microorganism belonging to coryneform bacteria includes the DNA described in EP 1108790 comprising the nucleotide sequence represented by SEQ ID NO:3.

"The region corresponding to a nucleotide sequence of positions 1,366 to 1,368 from the 5'-terminal of the nucleotide sequence represented by SEQ ID NO:3 in the nucleotide sequence of a DNA encoding ISOM derived from a microorganism belonging to coryneform bacteria" means a region which corresponds to a nucleotide sequence of positions 1,366 to 1,368 from the 5'-terminal of the nucleotide sequence represented by SEQ ID NO:3, on the nucleotide sequence of the DNA encoding ISOM derived from a microorganism belonging to coryneform bacteria, when homology of the nucleotide sequence in the DNA encoding ISOM derived from the coryneform bacterium with the nucleotide sequence represented by SEQ ID NO:3 is calculated by a homology analyzing program such as the above-described BLAST or FASTA, and the nucleotide sequences are aligned such that the homology between both nucleotide sequences becomes highest.

The DNA comprising a nucleotide sequence in which a region corresponding to a nucleotide sequence of positions 1,366 to 1,368 from the 5'-terminal of the nucleotide sequence represented by SEQ ID NO:3 is a codon encoding an amino acid residue other than a glycine residue can be obtained by introducing a nucleotide substitution into the DNA encoding ISOM derived from a microorganism belonging to coryneform bacteria according to the above-described site-directed mutagenesis.

The codon encoding an amino acid residue other than a glycine residue may be any codon, so long as it encodes an amino acid residue other than a glycine, and is preferably an amino acid residue selected from the group consisting of L-alanine, L-valine, L-leucine, L-isoleucine, L-methionine, L-tryptophan, L-phenylalanine, L-proline, L-lysine, L-histidine, L-arginine, L-aspartic acid and L-glutamic acid residues, more preferably an L-aspartic acid or L-glutamic acid residue, and more preferably an L-aspartic acid residue.

Whether the DNA obtained in the above is the DNA of the present invention described in the above item (ii) can be confirmed by examining whether a coryneform bacterium obtained by transforming a coryneform bacterium capable of producing a wild type ISOM with the DNA, and substituting the DNA with a DNA encoding the wild type ISOM by a homologous recombination technique exhibits the above-described partial leucine requirement.

The DNAs in the above-described items (vi) to (viii) can be obtained by applying the above-described side-directed mutagenesis to a DNA comprising the nucleotide sequence represented by SEQ ID NO:3 to thereby substitute the nucleotide sequence of positions 1,366 to 1,368 from the 5'-terminal of the nucleotide sequence represented by SEQ ID NO:3 with a codon encoding an amino acid residue other than a glycine residue.

The codon encoding an amino acid residue other than a glycine residue may be any codon, so long as it encodes an amino acid residue other than a glycine, and is preferably a codon encoding an amino acid residue selected from the group consisting of L-alanine, L-valine, L-leucine, L-isoleucine, L-methionine, L-tryptophan, L-phenylalanine, L-proline, L-lysine, L-histidine, L-arginine, L-aspartic acid and L-glutamic acid residues, more preferably a codon encoding an L-aspartic acid or L-glutamic acid residue, and most preferably a codon encoding an L-aspartic acid residue.

The DNA in which a nucleotide sequence of positions 1,366 to 1,368 from the 5'-terminal of the nucleotide sequence represented by SEQ ID NO:3 is substituted with a codon encoding an aspartic acid residue includes a DNA in which guanine at position 1,367 from the 5'-terminal of the nucleotide sequence is substituted with adenine.

Whether the DNA obtained in the above is the DNA of the present invention described in any one of the above-described items (vi) to (viii) can be confirmed by examining whether a coryneform bacterium obtained by transforming a coryneform bacterium capable of producing a wild type ISOM with the DNA, and substituting the DNA with a DNA encoding the wild type ISOM by a homologous recombination technique exhibits the above-described partial leucine requirement.

As to the DNA described in the above item (ix), "the DNA which is hybridizable with a DNA comprising a nucleotide sequence complementary to the nucleotide sequence represented by SEQ ID NO:3 under stringent conditions" means a DNA which can be obtained according to colony hybridization, plaque hybridization, Southern hybridization or the like by using a partial or full length of a complementary chain of DNA comprising the nucleotide sequence represented by SEQ ID NO:3, and specifically includes a DNA which can be identified by carrying out hybridization at 65° C. in the presence of 0.7 to 1.0 mo/l sodium chloride by using a filter to which colony- or plaque-derived DNAs are immobilized, and then washing the filter under conditions of 65° C. with a 0.1 to 2× concentration SSC solution (composition of 1×SSC solution comprising 150 mmol/l sodium chloride and 15 mmol/l sodium citrate). The hybridization can be carried out according to the method described in *Molecular Cloning*, Third Edition, *Current Protocols in Molecular Biology, DNA Cloning* 1: *Core Techniques, A Practical Approach*, Second Edition, Oxford University (1995) or the like. The DNA which is hybridizable includes a DNA having a homology of at least 60% or more, preferably a DNA having a homology of 80% or more, and more preferably a DNA having a homology of 95% or more, with the nucleotide sequence represented by SEQ ID NO:3, when calculated by using the above-described BLAST, FASTA or the like based on the above-described parameters.

When the DNA obtained by the above-described method is a DNA comprising a nucleotide sequence in which a region corresponding to a nucleotide sequence of positions 1,366 to 1,368 from the 5'-terminal of the nucleotide sequence represented by SEQ ID NO:3 is a codon encoding an amino acid residue other than a glycine residue, whether the DNA obtained by the above-described method is the DNA of the present invention described in the above item (ix) can be confirmed by examining whether a coryneform bacterium obtained by transforming a coryneform bacterium capable of producing a wild type ISOM with the DNA, and substituting the DNA with a DNA encoding the wild type ISOM by a homologous recombination technique exhibits the above-described partial leucine requirement.

When the DNA obtained by the above-described method is a DNA comprising a nucleotide sequence in which a region corresponding to a nucleotide sequence of position 1,366 to 1,368 from the 5'-terminal of the nucleotide sequence represented by SEQ ID NO:3 is a codon encoding a glycine residue, the DNA of the present invention described in the above item (ix) can be obtained by introducing a site-directed mutation into the DNA obtained by the above-described method, according to the method for obtaining the DNA of the present invention described in the above item (ii).

Whether the DNA is the DNA of the present invention described in the above item (ix) can be confirmed by examining whether a coryneform bacterium obtained by transforming a coryneform bacterium capable of producing a wild type ISOM with the DNA, and substituting the DNA with a DNA encoding the wild type ISOM by a homologous recombination technique exhibits the above-described partial leucine requirement.

[3] Preparation of the DNA of the Present Invention
(i) Preparation of DNA Encoding Isopropylmalate Isomerase or ISOM Derived from microorganism belonging to coryneform bacteria As the method for preparing a DNA encoding isopropylmalate isomerase or ISOM derived from a microorganism belonging to coryneform bacteria, mentioned is a method in which the DNA is obtained by PCR or the like using a chromosomal DNA as the template which can be prepared according to the method of Saito et al. [*Biochim. Biophys. Acta*, 72, 619 (1963)] from a microorganism belonging to coryneform bacteria and using primer DNAs which can be designed and synthesized based on the nucleotide sequences represented by SEQ ID NOs:3 and 4 or the nucleotide sequence represented by SEQ ID NO:3.

Specifically, a chromosomal DNA is prepared from *Corynebacterium glutamicum* ATCC13032, DNAs having 5'-terminal and 3'-terminal regions of respective nucleotide sequences represented by SEQ ID NOs:3 and 4 are prepared by chemical synthesis, and PCR is carried out by using the DNA as the template and the DNAs as primer set to thereby prepare a DNA encoding isopropylmalate isomerase. Also, a DNA encoding ISOM can be obtained by carrying out PCR using DNAs having 5'-terminal and 3'-terminal regions of the nucleotide sequence represented by SEQ ID NO:3 as the primer set. The DNA which can be obtained by the above-described methods includes a DNA comprising the nucleotide sequences represented by SEQ ID NOs:3 and 4 and a DNA comprising the nucleotide sequence represented by SEQ ID NO:3.

Also, a DNA encoding isopropylmalate isomerase or ISOM derived from a microorganism belonging to coryneform bacteria can be obtained by a hybridization method using, as the probe, a partial or full length of a DNA comprising the nucleotide sequences represented by SEQ ID NOs:3 and 4 or the nucleotide sequence represented by SEQ ID NO:3.

Furthermore, the DNA encoding isopropylmalate isomerase or ISOM derived from a microorganism belonging to coryneform bacteria can be obtained based on the nucleotide sequences represented by SEQ ID NOs:3 and 4 or the nucleotide sequence represented by SEQ ID NO:3, by chemically synthesizing the DNA comprising the nucleotide sequence(s) according to the usual method.

(ii) Preparation of the DNA of the Present Invention

The DNA of the present invention can be obtained by introducing a site-directed mutation into the DNA obtained in the above-described item (i) encoding isopropylmalate isomerase or ISOM derived from a microorganism belonging to coryneform bacteria, according to the method described in *Molecular Cloning*, Third Edition, *Current Protocols in Molecular Biology*, or the like.

When the DNA obtained in the above-described item (i) comprises a nucleotide sequence in which a region corresponding to the nucleotide sequence of positions 1,366 to 1,368 from the 5'-terminal of the nucleotide sequence represented by SEQ ID NO:3 is a codon encoding an amino acid residue other than a glycine residue, the DNA is the DNA of the present invention.

Also, the DNA of the present invention can be obtained according to a known method by chemically synthesizing a DNA comprising the nucleotide sequence in which a region corresponding to a nucleotide sequence of positions 1,366 to 1,368 from the 5'-terminal of the nucleotide sequence represented by SEQ ID NO:3 is a codon encoding an amino acid residue other than a glycine residue, as a DNA obtained in the above-described item (1) encoding isopropylmalate isomerase or ISOM derived from a microorganism belonging to coryneform bacteria.

As the DNA of the present invention obtained in this manner, mentioned is a DNA comprising a nucleotide sequence in which the nucleotide at position 1,366 from the 5'-terminal of the nucleotide sequence represented by SEQ ID NO:3 is substituted with adenine, instead of guanine.

The DNA is a DNA encoding a polypeptide comprising an amino acid sequence in which the amino acid residue at position 456 from the N-terminal of the amino acid sequence represented by SEQ ID NO:1 is substituted with an L-asparagine residue, instead of a glycine residue.

[4] Production of the Polypeptide of the Present Invention

The polypeptide of the present invention can be produced by expressing the DNA of the present invention of the above [2] in a host cell by the methods described in *Molecular Cloning*, Third Edition, *Current Protocols in Molecular Biology*, and the like, for example, by the following method.

That is, if necessary, a DNA fragment containing a part encoding the protein and having an appropriate length is prepared based on the DNA obtained in the above, and a recombinant DNA in which the DNA fragment is inserted into downstream of the promoter of an appropriate expression vector is constructed. A transformant can be prepared by introducing the recombinant DNA into a host cell which is suitable for the expression vector.

Furthermore, the polypeptide of the present invention can be efficiently produced by preparing the DNA in which the nucleotide sequence of the DNA fragment is substituted with nucleotides which provide codons suitable for the expression of the host cell.

As the host cell, any host cell can be used, so long as it is a bacterium cell or a yeast cell which can express the gene of interest. As the expression vector, a vector which can autonomously replicate in the above host cell or can be integrated into the chromosome and has a promoter at such a position that the DNA encoding the polypeptide of the present invention can be transcribed is used.

When a prokaryotic such as a bacterium is used as the host cell, it is preferred that the expression vector containing the DNA encoding the polypeptide of the present invention can autonomously replicate in the prokaryotic and is a vector comprising a promoter, a ribosome binding sequence, the DNA of the present invention, and a transcription termination sequence. A gene which controls the promoter can also be contained.

The expression vector includes pBTrp2, pBTac1 and pBTac2 (all available from Boehringer-Mannheim), pKK233-2 (manufactured by Pharmacia), pSE280 (manufactured by Invitrogen), pGEMEX-1 (manufactured by Promega), pQE-8 (manufactured by QIAGEN), pKYP10 (Japanese Published Unexamined Patent Application No. 110600/83), pKYP200 [*Agric. Biol. Chem.*, 48 669 (1984)], pLSA1 [*Agric. Biol. Chem.*, 53, 277 (1989)], pGEL1 [*Proc. Natl. Acad. Sci. USA*, 82, 4306 (1985)], pBluescript II SK(-) (manufactured by Stratagene), pTrs30[prepared from *Escherichia coil* JM109/pTrS30 (FERM BP-5407)], pTrs32 [prepared from *Escherichia coil* JM109/pTrS32 (FERM BP-5408)], pGHA2 [prepared from *Escherichia coil* IGHA2 (FERM BP-400), Japanese Published Unexamined Patent Application No. 221091/85], pGKA2 [prepared from *Escherichia coil* IGKA2 (FERM BP-6798), Japanese Published Unexamined Patent Application No. 221091/85], pTerm2 (US4686191, US4939094, US5160735), pSupex, pUB110, pTP5, pC194, pEG400 [*J. Bacteriol.*, 172, 2392 (1990)], pGEX (manufactured by Pharmacia), pET system (manufactured by Novagen), and the like.

As the promoter, any promoter can be used, so long as it can function in the host cell. Examples include promoters derived from *Escherichia coli*, phage, and the like, such as trp promoter (Ptrp), lac promoter, $P_L$ promoter, $P_R$ promoter and T7 promoter. Furthermore, artificially designed and modified promoters such as a promoter in which two Ptrp are linked in tandem (Ptrp×2), tac promoter, lacT7 promoter, letI promoter and the like can also be used. A plasmid in which the space between the Shine-Dalgarno sequence and initiation codon is controlled at an appropriate distance (e.g., 6 to 18 nucleotides) is preferably used. Although a transcription termination sequence is not always necessary for the expression of the DNA of the present invention in the vector of the present invention, the transcription termination sequence is preferably arranged just below the structural gene.

The host cell includes microorganisms belonging to the genus *Escherichia*, the genus *Serratia*, the genus *Bacillus*, the genus *Brevibacterium*, the genus *Corynebacterium*, the genus *Microbacterium*, the genus *Pseudomonas* and the like, such as *Escherichia coli* XL1-Blue, *Escherichia coli* XL2-Blue, *Escherichia coli* DH1, *Escherichia coli* MC1000; *Escherichia coli* KY3276, *Escherichia coli* W1485, *Escherichia coli* JM109, *Escherichia coli* HB101, *Escherichia coli* No.49, *Escherichia coli* W3110, *Escherichia coli* NY49, *Escherichia coli* GI698, *Escherichia coli* TB1, *Serratia ficaria*, *Serratia fonticola*, *Serratia liquefaciens*, *Serratia marcescens*, *Bacillus subtilis*, *Bacillus amyloliquefaciens*, *Brevibacterium roseum*, *Brevibacterium thiogenitalis*, *Brevibacterium immariophilum*, *Brevibacterium ammoniagenes*, *Brevibacterium immariophilum* ATCC14068, *Brevibacterium saccharolyticum* ATCC14066, *Brevibacterium flavum* ATCC14067, *Brevibacterium lactofermentum* ATCC13869, *Corynebacterium acetoacidophilum*, *Corynebacterium cal*-

*lunae, Corynebacterium glutamicum* ATCC13032, *Corynebacterium glutamicum* ATCC13869, *Corynebacterium acetoacidophilum* ATCC13870, *Corynebacterium callunae, Corynebacterium herculis, Corynebacterium lilium, Corynebacterium melassecola, Corynebacterium thermoaminogenes, Microbacterium ammoniaphilum* ATCC15354, *Pseudomonas putida*, and *Pseudomonas* sp. D-0110.

Particularly, preferred host cells are microorganisms belonging to coryneform bacteria, such as *Corynebacterium acetoacidophilum, Corynebacterium acetoglutamicum, Corynebacterium callunae, Corynebacterium glutamicum, Corynebacterium lactofermentum, Corynebacterium herculis, Corynebacterium lilium, Corynebacterium melassecola, Corynebacterium thermoaminogenes, Brevibacterium saccharolyticum, Brevibacterium immariophilum, Brevibacterium roseum, Brevibacterium thiogenitalis*, and *Microbacterium ammoniaphilum*.

More specifically, preferred host cells are *Corynebacterium acetoacidophilum* ATCC13870, *Corynebacterium acetoglutamicum* ATCC15806, *Corynebacterium callunae* ATCC15991, *Corynebacterium glutamicum* ATCC13032, *Corynebacterium glutamicum* ATCC13060, *Corynebacterium glutamicum* ATCC13826 (prior genus and species: *Brevibacterium flavum*), *Corynebacterium glutamicum* ATCC14020 (prior genus and species: *Brevibacterium divaricatum*), *Corynebacterium glutamicum* ATCC13869 (prior genus and species: *Brevibacterium lactofermentum*), *Corynebacterium herculis* ATCC13868, *Corynebacterium lilium* ATCC15990, *Corynebacterium melassecola* ATCC17965, *Corynebacterium thermoaminogenes* ATCC9244, ATCC9245, ATCC9246 and ATCC9277, *Brevibacterium saccharolyticum* ATCC14066, *Brevibacterium immariophilum* ATCC14068, *Brevibacterium roseum* ATCC13825, *Brevibacterium thiogenitalis* ATCC19240, and *Microbacterium ammoniaphilum* ATCC15354.

When the host cell is a microorganism belonging to the above genus *Corynebacterium*, the genus *Brevibacterium*, or the genus *Microbacterium*, the vector used for the preparation of the recombinant DNA containing the DNA of the present invention is preferably pCG1 (Japanese Published Unexamined Patent Application No. 134500/82), pCG2 (Japanese Published Unexamined Patent Application No. 35197/83), pCG4 (Japanese Published Unexamined Patent Application No. 183799/82), pCG11 (Japanese Published Unexamined Patent Application No. 134500/82), pCG116, pCE54 or pCB101 (all described in Japanese Published Unexamined Patent Application No. 105999/83), pCE51, pCE52 or pCE53 [all described in *Molecular and General Genetics*, 196, 175 (1984)], or the like.

As the method for introducing the recombinant vector, any method can be used, so long as it is a method in which the DNA is introduced into the above host cell. Examples include a method which uses calcium ion [*Proc. Natl. Acad. Sci. USA*, 69, 2110 (1972)], protoplast method (Japanese Published Unexamined Patent Application No. 186492/82, Japanese Published Unexamined Patent Application No. 18649/82), electroporation [for example, *Journal of Bacteriology*, 175, 4096 (1993), Appl. *Microbiol. Biotechnol.*, 52, 541 (1999)], methods described in *Gene*, 17, 107 (1982) and *Molecular & General Genetics*, 168, 111 (1979), and the like.

When yeast is used as the host cell, YEp13 (ATCC37115), YEp24 (ATCC37051), YCp50 (ATCC37419), pHS19, pHS15 or the like can be used as the expression vector.

As the promoter, any promoter can be used, so long as it can function in the yeast. Examples include a promoter of a gene in the glycolytic pathway such as hexose kinase, PHO5 promoter, PGK promoter, GAP promoter, ADH promoter, gall promoter, gal10 promoter, heat shock protein promoter, MFα1 promoter, and CUP1 promoter.

The host cell includes microorganisms belonging to the genus *Saccharomyces*, the genus *Schizosaccharomyces*, the genus *Kluyveromyces*, the genus *Trichosporon*, the genus *Schwanniomyces*, the genus *Pichia*, the genus *Candida* and the like, such as *Saccharomyces cerevisiae, Schizosaccharomyces pombe, Kluyveromyces lactis, Trichosporon pullulans, Schwanniomyces alluvius*, and *Candida utilis*.

As the method for introducing the recombinant vector, any method can be used, so long as it is a method for introducing DNA into yeast. Examples include electroporation [*Methods Enzymol.*, 194, 182 (1990)], spheroplast method [Proc. Natl. Acad. Sci. USA, 75, 1929 (1978)], lithium acetate method [*J. Bacteriol.*, 153, 163 (1983)], a method described in *Proc. Natl. Acad. Sci. USA*, 75, 1929 (1978) and the like.

When expression is carried out by using yeast, a glycosylated or sugar chain-added polypeptide can be obtained.

In the production of the polypeptide of the present invention, the polypeptide can be produced so as to have a structure as it is or can be produced as a secretory or fusion protein according to the method described in *Molecular Cloning*, Third Edition or the like.

The polypeptide of the present invention can be prepared by culturing the transformant obtained by the above method in a medium to produce and accumulate the polypeptide of the present invention in the culture and recovering the polypeptide of the present invention from the culture.

The transformant can be cultured according to the usual culturing method.

As the medium, any of natural medium or synthesized medium can be used, so long as, as the medium for culturing the transformant, it contains carbon sources, nitrogen sources, inorganic salts and the like which can be assimilated by the transformant and can efficiently culture the transformant.

The carbon sources include carbohydrates such as glucose, fructose, sucrose, maltose, and starch hydrolysate; alcohols such as ethanol; organic acids such as acetic acid, lactic acid, and succinic acid; and the like.

The nitrogen sources include ammonia, various inorganic or organic ammonium salts such as ammonium chloride, ammonium sulfate, ammonium carbonate, and ammonium acetate; urea; other nitrogen-containing compounds; nitrogen-containing organic materials, such as meat extract, yeast extract, corn steep liquor, and soybean hydrolysate; and the like.

The inorganic salts include potassium dihydrogen phosphate, dipotassium hydrogen phosphate, ammonium sulfate, sodium chloride, manganese sulfate, calcium carbonate, and the like.

In addition, if necessary, trace nutrients such as biotin and thiamin can be added. These trace nutrients can be substituted with medium additives such as meat extract, yeast extract, corn steep liquor, soybean hydrolysate and casamino acid.

Culturing is carried out under aerobic conditions, for example, by shaking culture or submerged spinner culture under aeration. The culturing temperature is preferably from 20 to 42° C., and more preferably from 30 to 40° C. The pH of the medium is preferably maintained at 5 to 9. The pH is adjusted with an inorganic or organic acid, an alkali solution, urea, calcium carbonate, ammonia or the like. The culturing term is generally from 1 to 6 days. Also, if necessary, antibiotics such as ampicillin and tetracycline can be added to the medium during the culturing.

When a microorganism transformed with a recombinant vector comprising an inductive promoter as the promoter is cultured, an inducer can be added to the medium, if necessary. For example, isopropyl-β-D-thiogalactopyranoside or the like can be added when a microorganism transformed with a recombinant vector comprising lac promoter is cultured, or indoleacrylic acid or the like can be added to the medium when a microorganism transformed with a recombinant vector comprising trp promoter is cultured.

As the process for producing the polypeptide of the present invention, mentioned are a process wherein the polypeptide is produced inside the host cell, a process wherein the polypeptide is secreted into the outside of the host cell, and a process wherein the polypeptide is produced on an outer membrane of the host cell, and depending on the method to be selected, the host cell used or the structure of the polypeptide produced are suitably changed.

When the polypeptide of the present invention is produced in a host cell or on an outer membrane of the host cell, the produced polypeptide can be forcibly secreted extracellularly according to the method of Poleson et al. [*J. Biol. Chem.*, 264, 17619 (1989)], the method of Lowe et al. [*Proc. Natl. Acad. Sci. USA*, 86, 8227 (1989), *Genes Develop.*, 4, 1288 (1990)], or the methods described in Japanese Published Unexamined Patent Application No. 336963/93, WO 94/23021 and the like.

Specifically, the polypeptide of the present invention can be forcibly secreted extracellularly by expressing it in a form that a signal peptide has been added to the upstream of a polypeptide containing the active region of the polypeptide of the present invention, using genetic engineering techniques.

Furthermore, according to the method described in Japanese Published Unexamined Patent Application No. 227075/90, the production can be increased by utilizing a gene amplification system which uses a dihydrofolate reductase gene or the like.

The polypeptide produced by the transformant of the present invention can be isolated and purified by a method generally used for isolating and purifying enzymes.

For example, when the polypeptide of the present invention is accumulated in a dissolved state in the cells, the cells are recovered by centrifugation after the culturing is finished, the cells are suspended in an aqueous buffer, and then the cells are disrupted using an ultrasonic oscillator, a French press, a Manton Gaulin homogenizer, a dynomill or the like to obtain a cell-free extract. The cell-free extract is centrifuged to obtain a supernatant, and a purified product can be obtained by subjecting the supernatant to a method generally used for isolating and purifying enzymes, that is, techniques, such as solvent extraction; salting out and desalting with ammonium sulfate or the like; precipitation with an organic solvent; anion exchange chromatography using a resin such as diethylaminoethyl (DEAE)-Sepharose or DIAION HPA-75 (manufactured by Mitsubishi Chemical); cation exchange chromatography using a resin such as S-Sepharose FF (manufactured by Pharmacia); hydrophobic chromatography using a resin such as butyl-Sepharose or phenyl-Sepharose; gel filtration using a molecular sieve; affinity chromatography; chromatofocusing; and electrophoresis such as isoelectric focusing, alone or in combination.

Also, when the polypeptide is produced in the cells in the form of an inclusion body, the cells are recovered, disrupted and centrifuged in the same manner to recover the inclusion body of the polypeptide as the precipitated fraction. The recovered inclusion body of the polypeptide is solubilized with a protein-denaturing agent. The polypeptide is made into normal higher-order structure by diluting or dialyzing the solubilized solution to decrease the concentration of the protein-denaturing agent in the solubilized solution. After this procedure, a purified product of the polypeptide can be obtained by the isolation and purification method similar to the above.

When the polypeptide of the present invention or its derivative such as the polypeptide to which a sugar chain is added is secreted extracellularly, the polypeptide or the polypeptide derivative can be recovered in the culture supernatant. Specifically, the culture supernatant is obtained by treating the culture with techniques such as centrifugation similar to the above, and a purified product can be obtained from the culture supernatant according to the isolation and purification method similar to the above.

As the polypeptide thus obtained, mentioned are the polypeptides described in the above [1], more specifically, a polypeptide in which a glycine residue at position 456 from the N-terminal of the amino acid sequence represented by SEQ ID NO:1 is substituted with an asparagine residue.

[5] Process for Producing L-Amino Acid of the Present Invention (i) Microorganism of the present invention As the microorganism of the present invention, mentioned are a microorganism which produces the protein of the present invention as the sole isopropylmalate isomerase and a microorganism which produces the protein of the present invention as the sole ISOM.

As the above-described microorganism, any microorganism may be used, so long as it is capable of producing the protein of the present invention as the sole isopropylmalate isomerase or ISOM, and is preferably a microorganism belonging to coryneform bacteria, more preferably a microorganism belonging to the genus *Corynebacterium*, the genus *Brevibacterium* or the genus *Microbacterium*, and furthermore preferably *Corynebacterium glutamicum*.

The microorganism of the present invention can be obtained by transforming a host cell with the DNA of the present invention according to the usual method.

When a plasmid obtained by ligating the DNA of the present invention to an autonomous replicable plasmid is used in the transformation, a microorganism which does not produce isopropylmalate isomerase or ISOM can be used as the host cell.

The microorganism which does not produce isopropylmalate isomerase or ISOM can be obtained according to the method described, for example, in *Appl. Microbiol. Biotechnol.*, 37, 566 (1992).

Also, the microorganism of the present invention can be obtained by introducing a site-directed mutation into a DNA encoding a wild type isopropylmalate isomerase or ISOM on the chromosomal DNA of a microorganism capable of producing isopropylmalate isomerase or ISOM according to the usual mutation treatment method, a gene substitution method using recombinant DNA technique, a cell fusion method, a transduction method or the like. The site-directed mutation can be introduced according to the method described in *Molecular Cloning*, Third Edition, *Current Protocols in Molecular Biology*, or the like.

As the method for preparing the microorganism of the present invention by recombinant DNA techniques, mentioned is a method which uses a recombinant plasmid obtained by introducing the DNA of the present invention prepared by the method of the above-described [2] into a plasmid which cannot autonomously replicate in the host microorganism and has an antibiotics-resistant marker gene and a levan sucrase gene sacB of *Bacillus subtilis* [*Mol. Microbiol.*, 6, 1195 (1992)].

The recombinant plasmid can be introduced into the host microorganism according to the method of the above-described [3].

Since the recombinant plasmid cannot autonomously replicate in the host microorganism, a microorganism in which the recombinant plasmid is integrated into the chromosome by Campbell type homologous recombination can be obtained by selecting the microorganism showing resistance to the antibiotic based on the antibiotics-resistant gene existing on the recombinant plasmid.

Next, a microorganism in which a DNA encoding the isopropylmalate isomerase or ISOM on the chromosomal DNA of a host microorganism is substituted with the DNA of the present invention can be obtained by carrying out selection which uses production of a suicide substrate by the levan sucrase of *Bacillus subtilis* [*J. Bacteriol.*, 174, 5462 (1992)] to be integrated into the chromosome together with the DNA of the present invention.

Although the gene replacement on the chromosomal DNA can be carried out by the above methods, not only the above methods but also other gene substitution methods can be used, so long as they can replace genes on the chromosome.

As a method for the preparation of transformants comprising the DNA of the present invention on the chromosomal DNA, a cell fusion method and a transduction method can be exemplified in addition to the above-described methods. For example, the methods described in *Amino Acid Fermentation*, edited by Hiroshi Aida, published by Japan Scientific Societies Press (1986) are mentioned.

(2) Production of L-amino Acid

An L-amino acid can be produced by culturing the microorganism obtained in the above-described item (1) in a medium to produce and accumulate the L-amino acid in the culture, and recovering the L-amino acid from the culture.

The method for culturing the microorganism is the same as the method for culturing the transformant of the above-described [3].

After completion of the culturing, the L-amino acid of interest can be isolated and purified from the culture obtained by removing the precipitate such as cells according to the usual method such as activated carbon treatment and ion exchange resin treatment.

The L-amino acid which can be produced in the present invention is not particularly limited, so far as it is an L-amino acid, and is preferably L-lysine, L-threonine, L-glutamine, L-arginine, L-proline, L-tryptophan, glycine, L-alanine, L-glutamic acid, L-asparagine, L-aspartic acid, L-methionine, L-valine, L-leucine, L-isoleucine, L-cysteine, L-phenylalanine, L-serine, L-histidine, L-tyrosine or L-ornithine, more preferably L-lysine, L-threonine, L-glutamine, L-arginine, L-proline, L-tryptophan, L-isoleucine or L-ornithine, and more preferably L-lysine, L-threonine, L-glutamine, L-arginine, L-proline or L-tryptophan.

Examples of the present invention are shown below, although the present invention is not limited to these examples.

BEST MODE FOR CARRYING OUT THE INVENTION

EXAMPLE 1

Preparation of Plasmid pCleuC456 for ISOM Gene Replacement:

A DNA encoding a polypeptide having an amino acid sequence in which the glycine residue at position 456 from the N-terminal of the amino acid sequence represented by SEQ ID NO:1 was substituted with an aspartic acid residue (Gly456Asp) was obtained in the following manner by site-directed mutagenesis using PCR (*Molecular Cloning*, Third Edition).

First, a chromosomal DNA of *Corynebacterium glutamicum* wild strain ATCC13032 was prepared according to the method of Saito et al. [*Biochim. Biophys. Acta,* 72, 619 (1963)].

Next, PCR was carried out by using the chromosomal DNA as the template and using a Pfu turbo DNA polymerase (manufactured by Stratagene), the buffer attached thereto and primers described below.

Based on the nucleotide sequence information of a known ISOM gene derived from *Cornybacterium glutamicum* (EP 1108790), a DNA fragment consisting of a nucleotide sequence in which a codon encoding a glycine residue was substituted with a codon (gac) encoding an aspartic acid residue (DNA consisting of the nucleotide sequence represented by SEQ ID NO:5) in a region consisting of 21 nucleotides (corresponding to positions 1359 to 1380 in SEQ ID NO:3) containing the region (ggc) encoding the glycine residue at position 456 from the N-terminal of the amino acid sequence (the amino acid sequence represented by SEQ ID NO:1) in ISOM encoded by the region (the nucleotide sequence represented by SEQ ID NO:3) encoding ISOM in the ISOM gene, and a DNA fragment consisting of the nucleotide sequence represented by SEQ ID NO:6 as its complementary sequence were synthesized by the usual method.

A DNA fragment consisting of 21 nucleotides of the 5'-terminal of the nucleotide sequence represented by SEQ ID NO:3 (DNA consisting of the nucleotide sequence represented by SEQ ID NO:7) and a DNA fragment consisting of 21 nucleotides as a complementary sequence of the nucleotide sequence of a gene at downstream of the 3'-terminal of the ISOM gene (DNA consisting of the nucleotide sequence represented by SEQ ID NO:8) were also synthesized.

Using a DNA consisting of the nucleotide sequence represented by SEQ ID NO:5 and a DNA consisting of the nucleotide sequence represented by SEQ ID NO:8, and a DNA fragment consisting of the nucleotide sequence represented by SEQ ID NO:6 and a DNA fragment consisting of the nucleotide sequence represented by SEQ ID NO:7, as respective primer sets, two PCR were carried out by using *Corynebacterium glutamicum* ATCC13032 chromosomal DNA as the template and using the Pfu turbo DNA polymerase (manufactured by Stratagene) and the buffer attached thereto.

Amplified products of about 1.4 kb and about 0.6 kb obtained by the PCR (a DNA fragment corresponding to the nucleotide sequence at positions 1 to 1,380 of the nucleotide sequence represented by SEQ ID NO:3 and a DNA fragment corresponding to the nucleotide sequence at position 1,360 to downstream of the C-terminal of the ISOM gene) were subjected to agarose gel electrophoresis and extracted and purified by using GENECLEAN Kit (manufactured by BIO 101).

PCR was further carried out by using both of the purified products as the templates and a DNA fragment consisting of the nucleotide sequence represented by SEQ ID NO:7 and a DNA fragment consisting of the nucleotide sequence represented by SEQ ID NO:8 as the primer set. By this PCR, a DNA fragment of about 2.0 kb in which the codon (ggc) encoding the glycine residue at position 456 from the N-terminal of the amino acid sequence in the ISOM represented by SEQ ID NO:1 was substituted with a codon (gac) encoding aspartic acid was obtained. The obtained DNA fragment of about 2.0 kb was subjected to agarose gel electrophoresis and then extracted and purified by using the GENECLEAN Kit.

Next, adenine was added to the 3'-terminal of the DNA fragment by reacting it with Taq polymerase (manufactured by Boehringer-Mannheim) at 72° C. for 10 minutes in the presence of dATP. The obtained DNA fragment of about 2.0 kb was inserted into a plasmid pESB30 by the TA cloning method (*Molecular Cloning*, Third Edition). The pESB30 is a plasmid prepared by linking a PstI DNA fragment of 2.6 kb containing a levan sucrase gene sacB derived from *Bacillus subtilis* [*Mol. Microbiol.*, 6, 1195 (1992)] to the PstI digestion site of vector pHSG299 containing a kanamycin-resistant gene [*Gene*, 61, 63 (1987)].

Specifically, pESB30 was digested with BamHI (manufactured by Takara Shuzo) and subjected to agarose gel electrophoresis, and then a pESB30 fragment was extracted and purified by using the GENECLEAN Kit. Both termini of the obtained pESB30 fragment were blunt-ended by using a DNA Blunting Kit (manufactured by Takara Shuzo) according to the protocol attached thereto. The blunt-ended pESB30 fragment was concentrated by phenol-chloroform extraction and ethanol precipitation, and then thymine was added to its 3'-terminal by reacting it with Taq polymerase (manufactured by Boehringer-Mannheim) at 70° C. for 2 hours in the presence of dTTP, and pESB30-T was thus prepared.

By mixing this pESB30-T fragment with the adenine-added DNA fragment of about 2.0 kb obtained in the above, the ligation reaction was carried out by using Ligation Kit ver 1 (manufactured by Takara Shuzo). Using the obtained reaction product, *Escherichia coli* DH5α (manufactured by TOYOBO) was transformed according to the usual method (*Molecular Cloning*, Third Edition).

The transformed cells were cultured on an LB agar medium [a medium prepared by dissolving 10 g of Bacto-Tryptone (manufactured by Difco), 5 g of yeast extract (manufactured by Difco), 10 g of sodium chloride and 16 g of Bacto-Agar (manufactured by Difco) in 1 liter of water and adjusting its pH to 7.0] containing 20 μg/ml kanamycin, and a transformant was selected. The selected transformant was cultured overnight in LB medium containing 20 μg/ml kanamycin, and a plasmid was prepared from the obtained culture by the alkaline SDS method (*Molecular Cloning*, Third Edition).

The obtained plasmid was subjected to a restriction enzyme digestion analysis, and it was confirmed that the plasmid is a plasmid having a structure in which the DNA fragment of about 2.0 kb obtained in the above was inserted into the pESB30. This plasmid was named pCleuC456.

EXAMPLE 2

Construction of L-Lysine-Producing Strain having the DNA of the present Invention:

Using the plasmid pCleuC456 prepared in Example 1, Gly456Asp mutation was introduced into the ISOM gene of an L-lysine-producing strain by a gene substitution method.

As the L-lysine-producing strain, *Corynebacterium glutamicum* AHP-3 (FERM BP-7382) whose genetic characters were known was used. The *Corynebacterium glutamicum* AHP-3 is a strain having an amino acid substitution mutation Val59Ala in the homoserine dehydrogenase gene (hom), an amino acid substitution mutation Thr33Ile in the aspartokinase gene (lysC) and an amino acid substitution mutation Pro458Ser in the pyruvate carboxylase gene (pyc) on the chromosome of the *Corynebacterium glutamicum* wild strain ATCC13032.

Mutation into ISOM gene of the L-lysine-producing strain AHP-3 by the gene substitution method was carried out by two recombination operations as shown below. Firstly, based on the inability of the plasmid pCleuC456 prepared in the above to perform autonomous replication in coryneform bacteria, strains of *Corynebacterium glutamicum* strain AHP-3 in which the plasmid was integrated into its chromosomal DNA by homologous recombination were respectively selected.

Specifically, kanamycin-resistant strains were selected by transforming the strain AHP-3 by electroporation according to the method of Rest et al. [*Appl. Microbiol. Biotech.*, 52, 541 (1999)]. The structure of the chromosome obtained from one of the selected kanamycin-resistant strains was examined by Southern hybridization (*Molecular Cloning*, Third Edition), and it was confirmed that the plasmid was integrated into the chromosome by Campbell type homologous recombination. In such a strain, wild type and mutation type ISOM genes are contiguously present on the chromosome so that the second homologous recombination is apt to occur between them.

The transformant (single recombinant) was spread on an SUC agar medium [a medium prepared by dissolving 100 g of sucrose, 7 g of meat extract, 10 g of peptone, 3 g of sodium chloride, 5 g of yeast extract (manufactured by Difco) and 18 g of bacto-agar (manufactured by Difco) in 1 liter of water and adjusting its pH to 7.2] and cultured at 30° C. for 1 day to select formed colonies. Since a strain having sacB gene converts sucrose into a suicide substrate, it cannot grow on the SUC agar medium [*J. Bacteriol.*, 174, 5462 (1991)]. On the other hand, a strain in which sacB gene is deleted by the second homologous recombination between wild type and mutation type ISOM genes being contiguously present on the chromosome can grow on this medium because it does not form the suicide substrate. In this second homologous recombination, either the wild type gene or the mutant gene is deleted together with the sacB gene. In the case of a strain in which the wild type gene is deleted together with the sacB gene, it means that a gene replacement into a mutation type occurred.

A chromosomal DNA was prepared from the obtained double recombinant by the method of Saito et al. [*Biochim. Biophys. Acta*, 72, 619 (1963)], and PCR was carried out by using a DNA fragment consisting of the nucleotide sequence represented by SEQ ID NO:3 and a DNA fragment consisting of the nucleotide sequence represented by SEQ ID NO:6 as the primer set and using Pfu turbo DNA polymerase (manufactured by Stratagene) and a buffer attached thereto. The nucleotide sequences of these PCR products were determined by the usual method to thereby examine whether the ISOM gene existing on the chromosomal DNA of the double recombinant was a wild type or a mutation type, and thus it was confirmed that a strain AHL-456 having the Gly456Asp mutation inside the ISOM gene was obtained.

EXAMPLE 3

L-Lysine production Test by ISOM Mutant Strain:

Each of the obtained strain AHL-456 and its parent strain AHP-3 was cultured at 30° C. for 24 hours by using a BYG agar medium (a medium prepared by dissolving 10 g of glucose, 7 g of meat extract, 10 g of peptone, 3 g of sodium chloride, 5 g of yeast extract and 18 g of Bacto-Agar in 1 liter of water and adjusting its pH to 7.2), and each of the strains was inoculated into a 2 liter capacity baffled conical flask containing 250 ml of a seed medium (a medium prepared by dissolving 50 g of sucrose, 40 g of corn steep liquor, 8.3 g of ammonium sulfate, 1 g of urea, 2 g of potassium dihydrogenphosphate, 0.83 g of magnesium sulfate heptahydrate, 10 mg of iron sulfate heptahydrate, 1 mg of copper sulfate pentahydrate, 10 mg of zinc sulfate heptahydrate, 10 mg of β-alanine, 5 mg of nicotinic acid, 1.5 mg of thiamine hydrochloride and 0.5 mg of biotin in 1 liter of water, adjusting its pH to 7.2 and then adding 30 g of calcium carbonate thereto) and cultured at 30° C. for 12 to 16 hours.

A total volume of the obtained seed culture was inoculated into a 5 liter capacity jar fermentor charged with 1,400 ml of a main culture medium (a medium prepared by dissolving 60 g of glucose, 20 g of corn steep liquor, 25 g of ammonium chloride, 2.5 g of potassium dihydrogenphosphate, 0.75 g of magnesium sulfate heptahydrate, 50 mg of iron sulfate heptahydrate, 13 mg of manganese sulfate pentahydrate, 50 mg of calcium chloride dihydrate, 6.3 mg of copper sulfate pentahydrate, 1.3 mg of zinc sulfate heptahydrate, 5 mg of nickel chloride hexahydrate, 1.3 mg of cobalt chloride hexahydrate, 1.3 mg of ammonium molybdate tetrahydrate, 14 mg of nicotinic acid, 23 mg of β-alanine, 7 mg of thiamine hydrochloride and 0.42 mg of biotin in 1 liter of water) and cultured under conditions of 34° C., 1 vvm and 800 rpm while adjusting the pH to 7.0 with aqueous ammonia.

When glucose in the medium was consumed, a glucose feed solution (a solution containing 400 g of glucose and 45 g of ammonium chloride in 1 liter of water) was continuously added. The feed solution was added in such a manner that the feeding rate became the same between the two strains, and the culturing was stopped when the culturing time reached 30 hours.

Cells were removed from the culture by centrifugation, and the accumulated amount of L-lysine hydrochloride in the supernatant was determined by high performance liquid chromatography (HPLC). The results are shown in Table 1.

TABLE 1

| Strain | Growth (OD660) | L-Lysine hydrochloride (g/l) |
|--------|----------------|------------------------------|
| AHP-3  | 81             | 78                           |
| AHL-456| 81             | 85                           |

As is apparent from Table 1, growth level of the strain AHL-456 having the DNA of the present invention did not change, but its L-lysine production efficiency was improved in comparison with the parent strain AHP-3.

EXAMPLE 4

Construction of L-Threonine-Producing Strain having the DNA of the Present Invention:

Using the pCleuC456 constructed in Example 1, the Gly456Asp mutation was introduced into ISOM gene of an L-threonine-producing strain by a gene substitution method as in Example 2.

As the L-threonine-producing strain, *Corynebacterium glutamicum* ATCC21660 was used. The strain ATCC21660 is a mutant strain obtained from *Corynebacterium glutamicum* wild strain ATCC13032 by inducing a methionine-requiring mutation, an α-amino-β-hydroxyvaleric acid (AHV)-resistant mutation and an S-(2-aminoethyl)-cysteine (AEC)-resistant mutation [*Agr. Biol. Chem.*, 36, 1611 (1972)].

Using the obtained chromosomal DNA of the double recombinant, PCR was carried out in the same manner as in Example 1 by using a DNA fragment consisting of the nucleotide sequence represented by SEQ ID NO:7 and a DNA fragment consisting of the nucleotide sequence represented by SEQ ID NO:8 as the primer set. The nucleotide sequence of the PCR product was determined by the usual method, and it was confirmed that a strain THC-15 having the Gly456Asp mutation in the ISOM gene was obtained.

EXAMPLE 5

L-Threonine Production Test by ISOM Mutant Strain:

Each of the strain THC-15 and its parent strain ATCC21660 was cultured at 30° C. for 24 hours on the BYG agar medium and then inoculated into a test tube charged with 10 ml of a seed medium (a medium prepared by dissolving 20 g of glucose, 10 g of peptone, 10 g of yeast extract and 2.5 g of sodium chloride in 1 liter of water and adjusting its pH to 7.4) and cultured at 30° C. for 24 hours. Next, 1 ml of the seed culture was inoculated into a test tube charged with 10 ml of a main culture medium (a medium prepared by dissolving 100 g of glucose, 5 g of corn steep liquor, 20 g of ammonium chloride, 0.5 g of dipotassium hydrogenphosphate, 0.5 g of potassium dihydrogenphosphate, 1 g of magnesium sulfate heptahydrate, 10 mg of iron sulfate heptahydrate, 10 mg of manganese sulfate pentahydrate, 0.1 mg of biotin and 0.1 mg of L-methionine in 1 liter of water, adjusting its pH to 7.4 and then adding 20 g of calcium carbonate thereto) and cultured at 30° C. for 72 hours.

Cells were removed from the culture by centrifugation, and the accumulated amount of L-threonine in the supernatant was determined by high performance liquid chromatography (HPLC). The results are shown in Table 2.

TABLE 2

| Strain    | Growth (OD660) | L-Threonine (g/l) |
|-----------|----------------|-------------------|
| ATCC21660 | 34             | 9.1               |
| THC-15    | 34             | 11.5              |

As is apparent from Table 2, growth level of the strain THC-15 having the DNA of the present invention did not change, but its L-threonine production efficiency was improved in comparison with the parent strain ATCC21660.

EXAMPLE 6

Construction of L-Glutamine-Producing Strain having the DNA of the Present Invention:

Using the pCleuC456 constructed in Example 1, the Gly456Asp mutation was introduced into the ISOM gene of an L-glutamine-producing strain by a gene substitution method as in Example 2.

As the L-glutamine-producing strain, a *Corynebacterium glutamicum* wild type strain ATCC14752 (Japanese Published Examined Patent Application No. 51112/87) was used.

Using the obtained chromosomal DNA of the double recombinant, PCR was carried out in the same manner as in Example 1 by using a DNA fragment consisting of the nucleotide sequence represented by SEQ ID NO:7 and a DNA fragment consisting of the nucleotide sequence represented by SEQ ID NO:8 as the primer set. The nucleotide sequence of the PCR product was determined by the usual method, and it was confirmed that a strain ASL-7 having the Gly456Asp mutation in the ISOM gene was obtained.

EXAMPLE 7

L-Glutamine Production Test by ISOM Mutant Strain:

Each of the strain ASL-7 and its parent strain ATCC14752 was cultured at 28° C. for 24 hours on the BYG agar medium. One loopful of the cultured cells were inoculated into a 300 ml capacity conical flask charged with 20 ml of a production medium (a medium prepared by dissolving 150 g of glucose, 50 g of ammonium chloride, 0.7 g of dipotassium hydrogenphosphate, 0.7 g of potassium dihydrogenphosphate, 0.5 g of magnesium sulfate heptahydrate, 20 mg of iron sulfate heptahydrate, 20 mg of manganese sulfate pentahydrate, 10 mg of zinc sulfate heptahydrate, 6 μg of biotin, 1 mg of thiamine hydrochloride and 5 g of meat extract in 1 liter of water, adjusting its pH to 7.2 and then adding 50 g of calcium carbonate thereto) and cultured at 28° C. for 96 hours.

Cells were removed from the culture mixture by centrifugation, and the accumulated amount of L-glutamine in the supernatant was determined by high performance liquid chromatography (HPLC). The results are shown in Table 3.

TABLE 3

| Strain | Growth (OD660) | L-Glutamine (g/l) |
|---|---|---|
| ATCC14752 | 27 | 42 |
| ASL-7 | 26 | 48 |

As is apparent from Table 3, difference in the growth level was hardly found in the strain ASL-7 having the DNA of the present invention, but its L-glutamine production efficiency was improved in comparison with the parent strain ATCC14752.

EXAMPLE 8

Construction of L-Arginine-Producing Strain having the DNA of the Present Invention:

Using the pCleuC456 constructed in Example 1, the Gly456Asp mutation was introduced into the ISOM gene of an L-arginine-producing strain by a gene substitution method as in Example 2.

As the L-arginine-producing strain, *Corynebacterium glutamicum* FERM P-3616 was used. The strain FERM P-3616 is a mutant strain obtained from a *Corynebacterium glutamicum* wild strain by inducing a D-serine-sensitive mutation, a D-arginine resistance mutation, an arginine hydroxamate-resistant mutation and a 6-azauracyl-resistant mutation (Japanese Published Unexamined Patent Application No. 257486/89).

Using the obtained chromosomal DNA of the double recombinant, PCR was carried out in the same manner as in Example 1 by using a DNA fragment consisting of the nucleotide sequence represented by SEQ ID NO:7 and a DNA fragment consisting of the nucleotide sequence represented by SEQ ID NO:8 as the primer set. The nucleotide sequence of the obtained PCR product was determined by the usual method, and it was confirmed that a strain AUL-6 having the Gly456Asp mutation in the ISOM gene was obtained.

EXAMPLE 9

L-Arginine Production Test by ISOM Mutant Strain

Each of the strain AUL-6 and its parent strain FERM P-3616 was cultured at 30° C. for 24 hours on the BYG agar medium and then inoculated into a thick test tube charged with 6 ml of a seed medium (a medium prepared by dissolving 20 g of glucose, 10 g of peptone, 10 g of yeast extract and 2.5 g of sodium chloride in 1 liter of water and adjusting its pH to 7.2) and cultured at 30° C. for 24 hours. Next, 2 ml of the seed culture broth was inoculated into a 300 ml capacity conical flask charged with 20 ml of a main culture medium (a medium prepared by dissolving 150 g of blackstrap molasses (as glucose), 5 g of corn steep liquor, 30 g of ammonium sulfate, 3 g of urea, 0.5 g of dipotassium hydrogenphosphate, 0.5 g of potassium dihydrogenphosphate and 0.25 g of magnesium sulfate dihydrate in 1 liter of water, adjusting its pH to 7.2 and then adding 30 g of calcium carbonate thereto) and cultured at 30° C. for 72 hours.

Cells were removed from the culture mixture by centrifugation, and the accumulated amount of L-arginine in the supernatant was determined by high performance liquid chromatography (HPLC). The results are shown in Table 4.

TABLE 4

| Strain | Growth (OD660) | L-Arginine (g/l) |
|---|---|---|
| FERM P-3616 | 37 | 22 |
| AUL-6 | 36 | 26 |

As is apparent from Table 4, difference in the growth level was hardly found in the strain AUL-6 having the DNA of the present invention, but its L-arginine production efficiency was improved in comparison with the parent strain FERM P-3616.

EXAMPLE 10

Construction of L-Proline-Producing Strain having the DNA of the Present Invention:

Using the pCleuC456 constructed in Example 1, the Gly456Asp mutation was introduced into the ISOM gene of an L-proline-producing strain by a gene substitution method as in Example 2.

As the L-proline-producing strain, *Corynebacterium glutamicum* NRRL B-15511 was used. The strain NRRL B-15511 is a mutant strain obtained from a *Corynebacterium glutamicum* wild strain by inducing a 6-mercaptoguanosine-resistant mutation (Japanese Published Examined Patent Application No. 7196/92).

Using the obtained chromosomal DNA of the double recombinant, PCR was carried out in the same manner as in Example 1 by using a DNA fragment consisting of the nucleotide sequence represented by SEQ ID NO:7 and a DNA fragment consisting of the nucleotide sequence represented by SEQ ID NO:8 as the primer set. The nucleotide sequence of the PCR product was determined by the usual method, and it was confirmed that a strain MGL-5 having the Gly456Asp mutation in the ISOM gene was obtained.

EXAMPLE 11

L-Proline Production Test by ISOM Mutant Strain:

Each of the strain MGL-5 and its parent strain NRRL B-15511 was cultured at 30° C. for 24 hours on the BYG agar medium and then inoculated into a thick test tube charged with 6 ml of a seed medium (a medium prepared by dissolving 10 g of glucose, 5 g of meat extract, 10 g of peptone, 3 g of yeast extract and 3 g of sodium chloride in 1 liter of water and adjusting its pH to 7.2) and cultured at 30° C. for 24 hours. Next, 2 ml of the seed culture broth was inoculated into a 300 ml capacity conical flask charged with 20 ml of a main culture medium (a medium prepared by dissolving 100 g of glucose, 20 g of corn steep liquor, 10 g of ammonium sulfate, 3 g of potassium dihydrogenphosphate, 0.5 g of magnesium sulfate heptahydrate, 10 mg of iron sulfate heptahydrate, 10 mg of nicotinic acid, 0.1 g of thiamine hydrochloride, 0.1 g of biotin and 20 g of sodium L-glutamate in 1 liter of water, adjusting its pH to 7.4 and then adding 30 g of calcium carbonate thereto) and cultured at 32° C. for 96 hours.

Cells were removed from the culture mixture by centrifugation, and the accumulated amount of L-proline in the supernatant was determined by high performance liquid chromatography (HPLC). The results are shown in Table 5.

TABLE 5

| Strain | Growth (OD660) | L-Proline (g/l) |
|---|---|---|
| NRRL B-15511 | 30 | 18 |
| MGL-5 | 30 | 22 |

As is apparent from Table 5, growth level of the strain MGL-5 having the DNA of the present invention did not change, but its L-proline production efficiency was improved in comparison with the parent strain NRRL B-15511.

EXAMPLE 12

Construction of L-Tryptophan-Producing Strain having the DNA of the Present Invention:

Using the pCleuC456 constructed in Example 1, the Gly456Asp mutation was introduced into the ISOM gene of an L-tryptophan-producing strain by a gene substitution method as in Example 2.

As the L-tryptophan-producing strain, *Corynebacterium glutamicum* FERM BP-1777 was used. The strain FERM BP-1777 is a mutant strain obtained from a *Corynebacterium glutamicum* wild strain by inducing L-phenylalanine and L-tyrosine-requiring mutations, various aromatic amino acid analogues-resistant mutations and a 3-bromopyruvic acid-sensitive mutation (Japanese Patent No. 2578488).

Using the obtained chromosomal DNA of the double recombinant, PCR was carried out in the same manner as in Example 1 by using a DNA fragment consisting of the nucleotide sequence represented by SEQ ID NO:7 and a DNA fragment consisting of the nucleotide sequence represented by SEQ ID NO:8 as the primer set. The nucleotide sequence of the PCR product was determined by the usual method, and it was confirmed that a strain BPL-31 having the Gly456Asp mutation in the ISOM gene was obtained.

EXAMPLE 13

L-Tryptophan Production Test by ISOM Mutant Strain:

Each of the strain BPL-31 and its parent strain FERM BP-1777 was cultured at 30° C. for 24 hours on the BYG agar medium and then inoculated into a test tube charged with 6 ml of a seed medium (a medium prepared by dissolving 20 g of glucose, 15 g of peptone, 15 g of yeast extract, 2.5 g of sodium chloride, 1 g of urea, 200 mg of L-phenylalanine and 200 mg of L-tyrosine in 1 liter of water and adjusting its pH to 7.2) and cultured at 30° C. for 24 hours. Next, 2 ml of the seed culture was inoculated into a 300 ml capacity conical flask charged with 20 ml of a main culture (a medium prepared by dissolving 60 g of glucose, 10 g of corn steep liquor, 20 g of ammonium sulfate, 0.5 g of dipotassium hydrogenphosphate, 0.5 g of potassium dihydrogenphosphate, 0.25 g of magnesium sulfate heptahydrate, 10 mg of manganese sulfate heptahydrate and 0.03 g of biotin in 1 liter of water, adjusting its pH to 7.2 and then adding 20 g of calcium carbonate thereto) and cultured at 30° C. for 72 hours.

Cells were removed from the culture mixture by centrifugation, and the accumulated amount of L-tryptophan in the supernatant was determined by high performance liquid chromatography (HPLC). The results are shown in Table 6.

TABLE 6

| Strain | Growth (OD660) | L-Tryptophan (g/l) |
|---|---|---|
| FERM BP-1777 | 23 | 7.5 |
| BPL-31 | 23 | 8.5 |

As is apparent from Table 6, growth level of the strain BPL-31 having the DNA of the present invention did not change, but its L-tryptophan production efficiency was improved in comparison with the parent strain FERM BP-1777.

INDUSTRIAL APPLICABILITY

According to the present invention, modified isopropylmalate isomerase or ISOM and a DNA encoding the same are obtained, and L-amino acids can be efficiently produced by using a microorganism having the DNA.

Free Text of Sequence Listing

SEQ ID NO:5—Explanation of artificial sequence: Synthetic DNA

SEQ ID NO:6—Explanation of artificial sequence: Synthetic DNA

SEQ ID NO:7—Explanation of artificial sequence: Synthetic DNA

SEQ ID NO:8—Explanation of artificial sequence: Synthetic DNA

The invention claimed is:

1. A microorganism expressing a polypeptide comprising an amino acid sequence in which the amino acid residue corresponding to the amino acid at position 456 from the N-terminus of the amino acid sequence of SEQ ID NO: 1 is substituted with L-aspartic acid in an amino acid sequence of isopropylmalate isomerase large subunit (ISOM) derived from a coryneform bacterium belonging to the genus Corynebacterium, the genus Brevibacterium or the genus Mycobacterium, wherein the amino acid sequence of ISOM has 95% or more homology with the amino acid sequence of SEQ ID NO:1.

2. A microorganism expressing a polypeptide comprising an amino acid sequence in which the amino acid residue at position 456 from the N-terminus of the amino acid sequence of SEQ ID NO:1 is substituted with L-aspartic acid.

3. An isolated DNA encoding a polypeptide comprising an amino acid sequence in which the amino acid residue corresponding to the amino acid at position 456 from the N-terminus of the amino acid sequence of SEQ ID NO:1 is substituted with L-aspartic acid in an amino acid sequence of isopropylmalate isomerase large subunit (ISOM) derived from a coryneform bacterium belonging to the genus Corynebacterium, the genus Brevibacterium or the genus Mycobacterium, wherein the amino acid sequence of ISOM has 95% or more homology with the amino acid sequence of SEQ ID NO:1.

4. An isolated DNA comprising a nucleotide sequence in which a region corresponding to the nucleotide sequence of positions 1,366 to 1,368 from the 5'-terminus of the nucleotide sequence of SEQ ID NO:3 in a nucleotide sequence of a DNA encoding ISOM derived from a coryneform bacteria belonging to the genus Corynebacterium, the genus Brevibacterium or the genus Mycobacterium is a codon encoding L-aspartic acid wherein the nucleotide sequence of the DNA encoding ISOM has 95% or more homology with the nucleotide sequence of SEQ ID NO:3.

5. An isolated DNA comprising a nucleotide sequence in which the nucleotide sequence of positions 1,366 to 1,368 from the 5'-terminus of the nucleotide sequence of SEQ ID NO:3 is a codon encoding L-aspartic acid.

6. A recombinant DNA which comprises the DNA according to claim 3.

7. A transformed microorganism which is transformed with the recombinant DNA according to claim 6.

8. A transformed microorganism which comprises the DNA according to claim 3 on its chromosomal DNA.

9. The microorganism according to claim 7, which is a microorganism belonging to the genus Corynebacterium, the genus Brevibacterium or the genus Mycobacterium.

10. The microorganism according to claim 9, wherein the microorganism belonging to the genus Corynebacterium is Corynebacterium glutamicum.

11. A process for producing an L-amino acid, which comprises culturing the microorganism according to claim 7 in a medium to produce and accumulate the L-amino acid in the culture, and recovering the L-amino acid from the culture.

12. The process according to claim 11, wherein the L-amino acid is an amino acid selected from the group consisting of L-lysine, L-threonine, L-glutamine, L-arginine, L-proline and L-tryptophan.

* * * * *